United States Patent [19]
Aggarwal

[11] Patent Number: 5,658,949
[45] Date of Patent: Aug. 19, 1997

[54] INHIBITION OF TUMOR NECROSIS FACTOR BY RETINOIC ACID

[75] Inventor: Bharat B. Aggarwal, Houston, Tex.

[73] Assignee: Research Development Foundation, Carson City, Nev.

[21] Appl. No.: 346,626

[22] Filed: Nov. 30, 1994

Related U.S. Application Data

[63] Continuation-in-part of Ser. No. 61,471, May 17, 1993, Pat. No. 5,457,129.

[51] Int. Cl.⁶ .................................................. A61K 31/445
[52] U.S. Cl. ...................... 514/557; 514/825; 514/895; 514/903
[58] Field of Search ................................... 514/557, 825, 514/895, 903

[56] References Cited

U.S. PATENT DOCUMENTS 5,434,173  7/1995  Chandraratna ........................... 514/354

OTHER PUBLICATIONS

Chemical Abstracts 106:194429; Trinchieri et al. (1987).

*Primary Examiner*—Kevin E. Weddington
*Attorney, Agent, or Firm*—Benjamin Aaron Adler

[57] ABSTRACT

A novel method of inhibiting production of two important mediators of cellular function, tumor necrosis factor and nitric oxide, and treating a pathophysiological state characterized by an undesirable production or level of tumor necrosis factor or nitric acid. The methods of the present invention employ retinoic acid compounds. The most preferred retinoic acid is all-trans-retinoic acid. Also provided is a method of inhibiting tumor necrosis factor receptors using retinoic acid-like compounds.

15 Claims, 18 Drawing Sheets

INHIBITION OF TUMOR NECROSIS FACTOR BY RETINOIC ACID

CROSS-REFERENCE TO RELATED APPLICATION

This application is a continuation in part of U.S. patent application Ser. No. 08/061,471, filed May 17, 1993 now U.S. Pat. No. 5,457,129.

BACKGROUND OF THE INVENTION

1. Field of the Invention

The present invention relates generally to the fields of immunology and the biochemistry of biological response modifiers. More specifically, the present invention relates to a novel method for the inhibition of tumor necrosis factor and nitric oxide production.

2. Description of the Related Art

For more than 50 years, retinoids (natural and synthetic analogues of vitamin A) have attracted great attention by researchers in dermatology, cancer research, and embryonal development. A principal biological effect of the retinoids is to inhibit the growth and/or induce differentiation of the target cells. However, the mechanism of action of retinoids in producing these biological effects is not well understood.

Macrophages play many roles in diverse physiological processes. Depending on the signal received, mononuclear phagocytes can differentiate and become competent to perform specific sets of functions. An appropriate balance between activation (stimulation) and suppression of macrophage functions is essential. For example, inappropriate regulation of activation, by virtue of excess stimulation or insufficient suppression, can lead to extensive tissue injury and damage. This tissue damage, at times, may be so destructive that the survival of the host is threatened. Sites of inflammation, containing mononuclear phagocytes, frequently exhibit extensive damage to normal cells and tissue. In addition, the mechanisms by which macrophages injure and destroy the replicating cells of microbial or neoplastic origin, can also be turned against host cells. Many of the observed biological responses to invasive stimuli, triggered by infectious or neoplastic diseases, are mediated by host-secreted cytokines, in particular, the secreted products of activated macrophages.

Retinoids have been shown by several investigators to modulate the growth and differentiation functions of mononuclear phagocytes. For example, ATRA has been shown to downregulate the production of interferon by phytohaemagglutinin or anti-thymocyte globulin stimulated lymphocytes. Both IL-1 and IL-3 production was induced in vitro in human peripheral blood mononuclear cells and murine WEHI-3 cell lines, respectively, in the presence of retinoic acid in a dose-dependent manner. More recently, an augmenting effect of retinoic acid and 13-cis retinoic acid on IL-1 production by murine keratinoyctes was observed. Induction of IL-1 receptors in EL-4 cells and IL-2 receptors on activated human thymocytes was observed following the culture of these cells in presence of retinoic acid. Furthermore, transforming growth factor (TGF-$\beta_1$) protein as well its receptor can both be induced in HL-60 (promyelocytic leukemia) cells following their differentiation with retinoids. On the other hand, retinoic acid has been shown to down modulate the transcription of epidermal growth factor-receptor in human epidermoid carcinoma ME180 cells. Similarly, high concentrations of ATRA inhibit the production of interferon by L-929 cells infected with New Castle-disease virus.

Tumor necrosis factor-$\alpha$ (TNF), a cytokine produced primarily by activated macrophages, has been implicated as an important mediator of the inflammatory response and plays an important role in cancer, cachexia, septic shock, immunomodulation and differentiation. TNF exerts these multiple effects by binding to specific receptors on target cells through two different TNF receptors with molecular masses of about 60 kDa (p60) and 80 kDa (p80). Although most cells express both receptors, their relative abundance varies among different cell types. The p60 form of the TNF receptor is more prevalent on epithelial cells, whereas the p80 receptor is more abundant on cells of myeloid origin.

Nitric oxide (NO−), a highly reactive free-radical produced by the activated macrophages, has emerged as another important mediator of inflammatory responses. TNF in combination with nitric oxide and/or other cytokines (such as interleukin-1 and interleukin-6) may bring about the tissue destruction observed in certain autoimmune diseases such as psoriasis, rheumatoid arthritis, osteoarthritis and other joint diseases.

The prior art remains deficient in the lack of effective methods of inhibiting the production of tumor necrosis factor and nitric oxide. Moreover, the prior art is deficient in the lack of an effective method to treat pathophysiological states characterized by undesirable levels of tumor necrosis factor or nitric oxide in the body.

SUMMARY OF THE INVENTION

It is, therefore, an object of the present invention to provide a method of inhibiting production of tumor necrosis factor.

A further object of the present invention is to provide a novel method for inhibiting nitric oxide.

Yet another object of the present invention is to provide a novel and effective method for treating pathophysiological states characterized by an undesirable level of tumor necrosis factor or nitric oxide in the body.

In order to achieve the above objects, there is provided one embodiment of the present invention, a method of inhibiting the production of tumor necrosis factor comprising the step of administering to an animal a pharmacologically effective dose of a retinoic acid compound.

In another embodiment of the present invention, there is provided a method of inhibiting tumor necrosis factor receptors, comprising the step of administering to an animal a pharmacologically effective dose of a retinoic acid compound.

In yet at other embodiment of the present invention, there is provided a method of treating a pathophysiological state in an animal, wherein said state is characterized by production of an undesirable level of tumor necrosis factor, comprising the step of administering a pharmacologically effective dose of a retinoic acid compound.

In still yet another embodiment of the present invention, there is provided a method of treating a pathophysiological state in an animal, wherein said state is characterized by production of an undesirable level of nitric oxide, comprising the step of administering a pharmacologically effective dose of a retinoic acid compound.

The present invention illustrates the effect of various retinoids on two important mediators of inflammation: TNF and nitric oxide production. The results obtained suggest that all-trans retionic acid (ATRA) was most potent of all the retinoids studied and at physiological and pharmacologically achievable dose levels (0.1–1.0 µM), it inhibited both the TNF and nitric oxide production by activated murine macrophages.

Other and further objects, features and advantages will be apparent from the following descriptions of the presently preferred embodiments in the invention which are given for the purpose of disclosure and when taken in conjunction with the accompanying drawings.

BRIEF DESCRIPTION OF THE DRAWINGS

The drawings are not necessarily to scale. Certain features of the invention may be exaggerated in scale or shown in schematic form in the interest of clarity and conciseness.

DETAILED DESCRIPTION OF THE INVENTION

Figure 1:
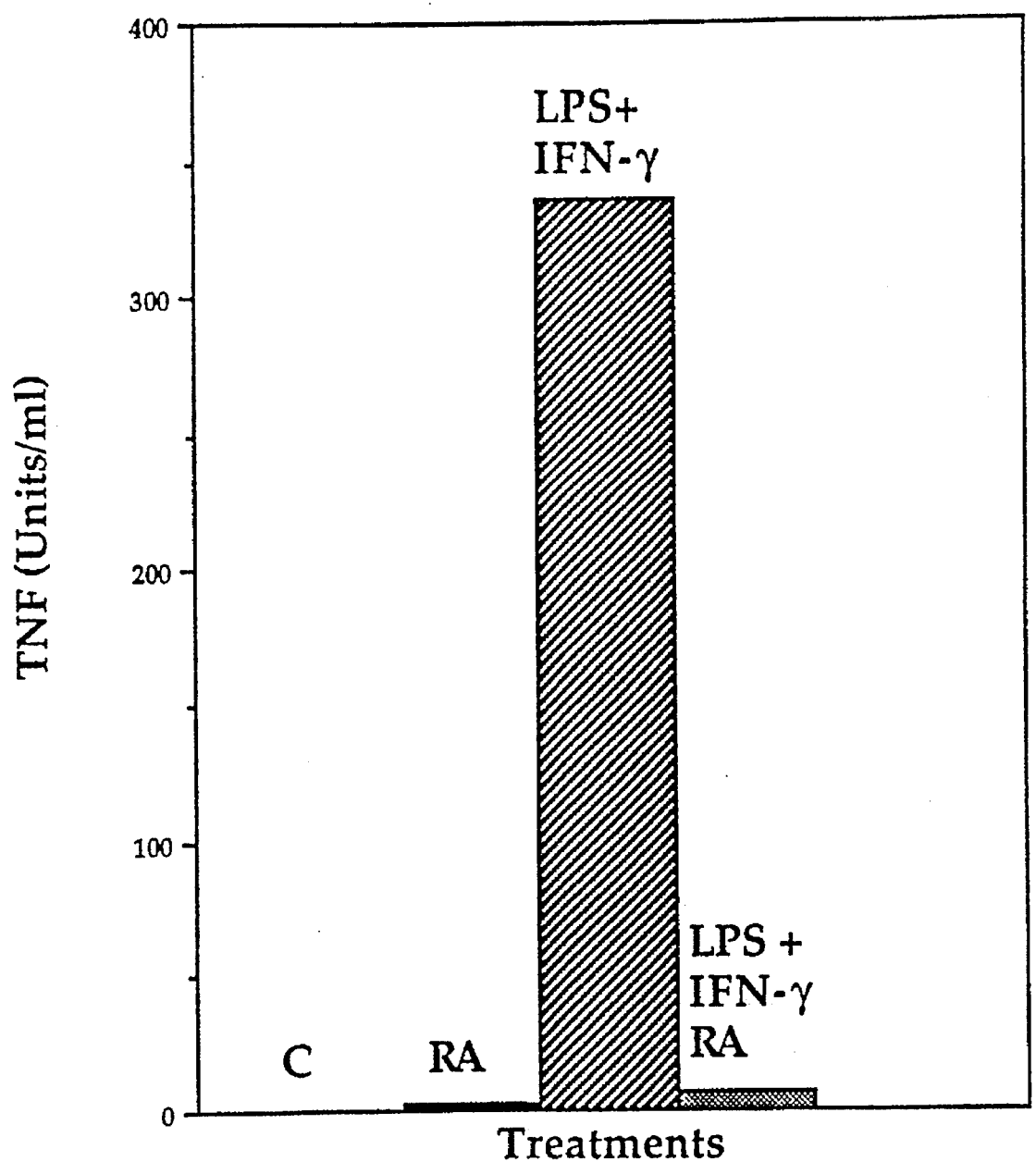
FIG. 1 shows the effect of in vitro all-trans retinoic acid (ATRA) treatment on TNF release by activated murine peritoneal macrophages. Two million macrophages were activated in 24-well plates with Interferon-g (IFN-g) (10 U/ml) and lipopolysaccharide (LPS) (100 ng/ml) in the presence or absence of ATRA (1 µM). Four hours later, cell-free supernatants were harvested and assayed for TNF activity as described in Example 1. The results shown represent one of four similar experiments.

The following abbreviations are occasionally used in describing the present invention: TNF, tumor necrosis factor; RA, all-trans retinoic acid; TTNPB, (E)-4-[2-(5, 6, 7, 8-tetrahydro-2-naphtalenyl)-1-propenyl]-benzoic acid; FBS, fetal bovine serum; AMF, autotrine motility factor; IL, interleukin; TGF, transforming growth factor; EGS, ethylene glycol-bis (succinimidyl succinate); BSA, bovine serum albumin; PBS, phosphate-buffered saline; EGF, epidermal growth factor; NGF, nerve growth factor; PkC, protein kinase C.

The present invention provides a method of inhibiting the production of tumor necrosis factor comprising the step of administering to an animal a pharmacologically effective dose of a retinoic acid compound. The present invention also provides a method of inhibiting the production of nitric oxide comprising the step of administering to an animal a pharmacologically effective dose of a retinoic acid compound.

In addition, the present invention also provides a method of treating a pathophysiological state in an animal, wherein said state is characterized by production of an undesirable level of tumor necrosis factor, comprising the step of administering a pharmacologically effective dose of a retinoic acid compound. Similarly, the present invention also provides a method of treating a pathophysiological state in an animal, wherein said state is characterized by production of an undesirable level of nitric oxide, comprising the step of administering a pharmacologically effective dose of a retinoic acid compound.

The present invention, in another embodiment, also provides a method of inhibiting tumor necrosis factor receptors, comprising the step of administering to an animal a pharmacologically effective dose of a retinoic acid compound. According to this method, the retinoic acid compound may be given to inhibit tumor necrosis factor receptor synthesis. Alternatively, a person having ordinary skill in this art may recognize that it may be more desirable to administer a retinoic acid compound to inhibit the amount of tumor necrosis factor receptors. As taught by the present invention, a retinoic acid compound may be used to inhibit either the p60 or the p80 form of the tumor necrosis factor receptor.

Generally, any retinoic acid compound which inhibits the production of tumor necrosis factor is useful in the methods of the present invention. More preferably, the retinoic acid compound is selected from the group consisting of all-trans-retinoic acid, 4-hydroxy-retinoic acid, 9-cis retinoic acid, (E)-4-[2-(5, 6, 7, 8-tetrahydro-2-naphtalenyl)-1-propenyl]-benzoic acid, 3-methyl-(E)-4-[2-(5, 6, 7, 8-tetrahydro-2-naphtalenyl)-1-propenyl]-benzoic acid and 13-cis-retinoic acid.

The methods of the present invention may be administered to any animal. Most preferably, the retinoic acid compounds useful in the methods of the present invention are administered to a human.

Generally, the dose of the retinoic acid compound given in the methods of the present invention is any that inhibits the production of tumor necrosis factor or nitric oxide in the animal. More preferably, the dose of the retinoic acid compound is between 10 nM and 1 μM.

Generally, the methods of treating a pathophysiological state of the present invention may be useful for any disease characterized by an undesirable level of tumor necrosis factor or nitric oxide production. Preferably, these methods are selected from the group consisting of sepsis, cachexia, neoplastic diseases such as Karposi's sarcoma, cerebral malaria, capillary leak syndrome and autoimmune disease. Representative autoimmune diseases include systemic lupus erythematosus, rheumatoid arthritis and multiple sclerosis. In addition, the methods of the present invention may be useful in the treatment of transplant rejection in humans.

The elevated levels of serum TNF in the circulation has been observed only under pathological conditions including bacterial, vital or parasitic infections, fever, cancer, autoimmune disorders, septic shock or under inflammatory conditions. The levels of TNF in serum may vary considerably based on the site of production and method of its determination. Since there are two different forms of TNF, i.e., membrane-associated form (molecular weight 26 kDa) and secreted form (molecular weight 17 kDa), the serum samples can determine only the latter form. The membrane-bound TNF is difficult to detect and requires histological or flow cytometric examination of the tissue. Thus the relevance of the circulating serum TNF concentrations in most pathological conditions has been questioned. The detection or lack of detection of circulating serum levels of TNF may not be adequate.

In most instances when TNF is secreted in the circulation, there is also a production of TNF inhibitor which is a soluble form of the TNF receptor. This inhibitor usually blocks the biological activity of TNF. Therefore, the determination of TNF levels by bioassay do not provide the true estimation of the levels of the cytokine. In most instances, immunoassays specific for TNF can be useful in circumventing this problem. Thus, the methods of the present invention to treat any of the above-mentioned pathophysiological states may be accomplished without an exact determination of the serum levels of TNF.

The dosage administered is dependent upon the age, weight, kind of concurrent treatment, if any, and nature of the pathophysiological state. The effective composition useful in the methods of the present invention may be employed in such forms as capsules, tablets, liposome encapsulations, liquid solutions, suspensions or elixirs for oral administration or sterile liquid forms such as solutions, suspensions or emulsions. Any inert carrier is preferably used, such as saline or phosphate buffered saline or any such carrier in which the compounds used in the methods of the present invention have suitable solubility properties.

The retinoic acid compounds useful in methods of the present invention may be administered in a pharmaceutically acceptable carrier. The pharmaceutically acceptable carrier is any solvent with which the retinoic acid compound is compatible and which is non-toxic to the individuals treated at the amounts administered. A pharmacological dose of the retinoic acid compound useful in the methods of the present invention is that amount which inhibits the production of tumor necrosis factor or nitric oxide.

The cell lines L-929 (Mouse connective tissue) and RAW 264.7 (murine macrophage) were obtained from American Type Culture Collection (Rockville, Md.). The cell lines tested negative for mycoplasma. The media and serum were screened for endotoxin by Limulus amebocyte lysate assay and were found to contain less than 0.25 ng/ml.

The following examples are given for the purpose of illustrating various embodiments of the methods of the present invention and are not meant to limit the present invention in any fashion.

EXAMPLE 1

Cell Culture

Murine L-929 and RAW 264.7 cell cultures were maintained in continuous exponential growth by weekly passages. Both cell lines were routinely grown in RPMI 1640 medium supplemented with glutamine (2 mM), 10% fetal calf serum, 10 mM Hepes buffer, and antibiotics (penicillin 100 U/ml and streptomycin 100 μg/ml) in a humidified incubator in 5% $CO_2$ in air.

EXAMPLE 2

Isolation of Mouse Macrophages

Resident peritoneal macrophages were obtained from mice by peritoneal lavage, using 5 ml ice-cold Dulbecco's phosphate buffered saline containing gentamicin (40 μg/ml) as described by Mehta et al., *J. Immunol.*, 136:4206–4212 (1986). Briefly, pooled cells were sedimented at 400× g for 10 minutes and were resuspended in medium to a concentration of $1.5 \times 10^6$/ml. One milliliter samples of the cell suspension were added per well to 2 cm$^2$ flat bottomed well tissue culture plates. The cells were incubated for 60 minutes at 37° C. in a 5% $CO_2$ air incubator. Non-adherent cells were removed by washing vigorously three time with warmed medium. Adherent cells ($10^6$ cells/2 ml/ well in 24-well plates) thus obtained were judged to be more than 95% macrophages by phagocytic uptake and nonspecific esterase staining.

During the exponential growth phase, RAW-264.7 cells were stimulated with the reagents indicated, in wells of a 24-well plate ($2 \times 10^6$ at 2 ml). At indicated time intervals, the cell-free supernatants were harvested and an aliquot was used immediately for TNF and nitric oxide determinations. A separate aliquot was stored at −80° C. for later use to determine the TNF protein using a murine TNF-ELISA kit.

EXAMPLE 3

Determination of TNF in Culture Supernatants

The cytotoxicity assays were carried out with $20 \times 10^3$ cells treated with actinomycin D (1 μg/ml) along with TNF for 24 hours. For this, cells were plated for overnight in 0.1 ml of the medium in 96-well Falcon plates. Thereafter, the medium was removed and a serial dilution of human TNF or assay supernatants was layered in 0.1 ml of the volume. After 24 hours of incubation at 37° C., the medium was removed and viable cells were monitored by crystal violet staining according to the procedure described by Leu et al. *J. Immunol* 147:1816 (1991). The percent of relative cell viability was calculated as optical density in the presence of test sample divided by optical density in the absence of test sample medium multiplied by 100. Murine TNF was measured from culture supernatants using a high sensitivity ELISA. Briefly cells were stained with 0.5% crystal violet in 20% methanol for 15 minutes at room temperature. Excess stain was removed under tap water and the plate was air dried. Stained cells were solubilized with Sorenson's buffer (0.1M sodium citrate in 5% ethanol, pH 4.2) and the absorbance of the solubilized dye was read at 540 nm on a Dynatech MR 5000 microplate reader. The percent relative cell viability was calculated as optical density in the presence of test sample divided by that of with the medium multiplied by 100.

Inhibitors of TNF activity can mask its activity. This can lead to underestimation of TNF by bioassays. Therefore, the ELISA assay (R & D System Inc.) was employed for the determination of TNF. This assay is highly quantitative, sensitive (sensitivity in picogram range) and specific. It employs the quantitative "sandwich" enzyme immunoassay technique. A monoclonal antibody specific for TNF was coated onto the microtiter plate for overnight. Then the samples were pipetted into the wells and the cytokine, if any, was captured by the immobilized antibody. After washing away any unbound sample proteins, an enzyme-linked polyclonal antibody specific for TNF was added to the wells and allowed to bind the cytokine bound during the first incubation. Following a wash to remove any unbound antibody-enzyme reagent, a substrate solution was added to the wells and color developed in proportion to the amount of cytokine bound in the initial step. Along with the samples to be tested, a series of wells were prepared using known concentrations of the TNF standards. A curve plotting the optical density versus the concentration of cytokine in these standard wells was prepared. By comparing the optical density of the samples to this standard curve, the concentration of the cytokine in the unknown samples is then calculated.

EXAMPLE 4

Measurement of Nitric Oxide

The amount of stable nitrite, the end product of nitric oxide generation by activated macrophages under different conditions, was determined by the method of Ding et al., *J. Immunol.* 145:940 (1990). Briefly, 50 μl of culture supernatant from control or LPS (100 ng/ml) and/or IFN-gamma(10 U/ML)-stimulated macrophages alone or cultured in presence of ATRA or supernatants from cell lines stimulated with phorbol myristic acetate (PMA, 20 ng/ml) were mixed with an equal volume of Griess reagent (1% sulfanilamide; 0.1% naphthylethylene diamine dihydrochloride; 2.5% $H_3PO_4$) at room temperature for 10 minutes. The absorbance at 550 nm was determined on a Vmax microplate reader. Nitrite in each test sample was determined by extrapolation from a sodium nitrite standard curve in each experiment.

EXAMPLE 5

Measurement of Transglutaminase Assay

Transglutaminase activity in cell lysates was assayed by determining $Ca^{++}$-dependent incorporation of tritiated-putrescine into dimethyl-casein at 37° C. as detailed by Mehta et al., (1986). Briefly, cells were washed three times in isotonic saline and were scraped from the dish in a minimal volume of 20 mM Tris-HCl, pH 7.6 containing 150 mM NaCl, 1 mM EDTA and 15 mM β-mercaptoethanol and were lysed by sonication. Tissue TGase activity in cell lysate was determined at 37° C. in a final volume of 100 μl reaction mixture containing 50 mM Tris-HCl, pH 7.5, 30 mM NaCl, 2 mg/ml N, N'-dimethylcasein, 10 mM dithiothreitol, 5 mM $CaCl_2$, 0.2 mM putrescine and 0.4 mM $^3$H-putrescine (specific activity 33.1 Ci/mmole). The enzyme activity was expressed as nanomoles of putrescine covalently incorporated into dimethylcasein per hour per milligram of cell protein. Protein content in cell extracts was determined by Biorad's Bradford reagent.

EXAMPLE 6

Effects of ATRA on TNF Production

FIG. 1 demonstrates that LPS (100 ng/ml) in combination with IFN-gamma ((10 U/ml) induces high TNF production in murine resident peritoneal macrophages as determined in a biological assay using L929 as target cells. The cytotoxic ability of culture supernatants from activated macrophages could be completely abolished by concomitant addition of a monospecific antibody against TNF during incubation with L929 cells. Co-culture of cells with ATRA during the activation phase resulted in a significant inhibition of TNF release. ATRA was most potent inhibitor of TNF production by activated macrophages, whereas retinaldehyde was completely inactive (Table 1). Other analogs of vitamin A inhibited TNF production in the following order: ATRA>4-hydroxy ATRA>13-cis retinoic acid>retinol (vitamin A)>retinaldehyde (Table 1).

TABLE I

Effect of Retinoic acid and its analogues on the LPS and IFN-g-dependent induction of Transgutaminase and TNF from murine peritoneal macrophages

| Treatment | Transglutaminase (cpm/μg/hour) | TNF (units/ml) |
|---|---|---|
| None | 165 ± 0 | not detectable |
| IFN-g + LPS | 291 ± 0 | 54 ± 14 |
| ATRA | 934 ± 25 | 0.9 ± 0.1 |
| 13 cis-RA | 1014 ± 60 | 35 ± 1.4 |
| Retinol | 184 ± 7 | 46 ± 2.8 |
| Retinaldehyde | 518 ± 0.16 | 54 ± 14 |
| 4-OH-ATRA | 1108 ± 10 | 29 ± 1.4 |
| Vitamin $D_3$ | 368 ± 0 | 46 ± 8 |

The ATRA-induced inhibitory effect on TNF production was a specific effect and not due to non-specific toxicity of the drug to the cells. Macrophages treated with ATRA showed no appreciable change in their morphology when compared to untreated control cells. Expression of transglutaminase, an enzyme that is specifically induced by ATRA in cultured macrophages, was elevated in presence of ATRA and other analogs (Table 1). DMSO, the vehicle used for delivering ATRA to the cultures, had no effect alone on TNF production by the activated macrophages. Moreover, addition of ATRA or DMSO to L929 cell cultures did not affect the ability of exogenously added TNF to kill these cells. ATRA-mediated suppression of TNF production by activated macrophages was dose-dependent and time-dependent.

Figure 2A:
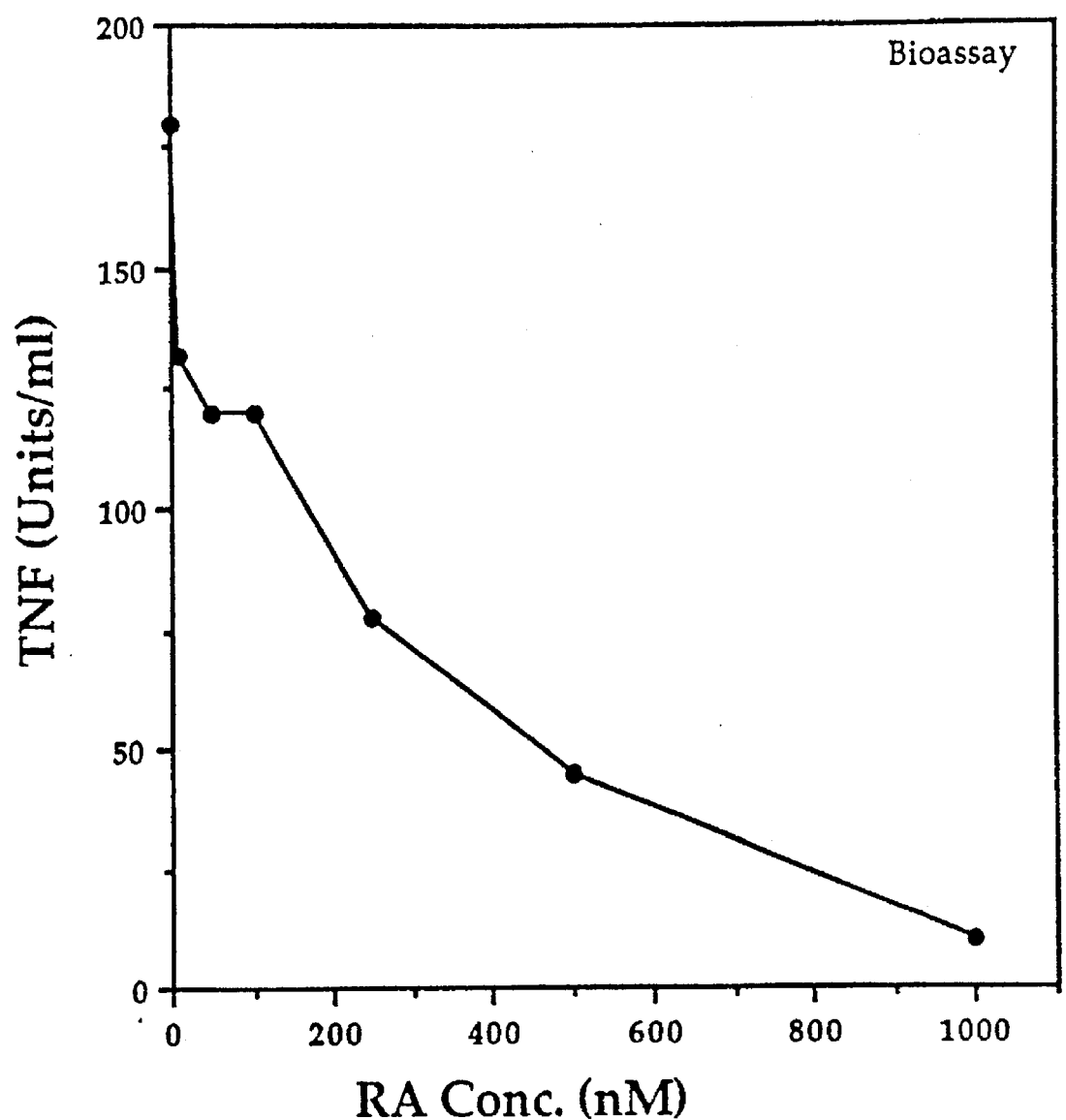
FIG. 2 shows the dose-dependent inhibition of TNF production by ATRA from peritoneal macrophages. Macrophage monolayers were activated by IFN-g+LPS in the presence of indicated ATRA dose levels. Four hour cell-free supernatants were analyzed for TNF either by using L929 cells as targets (FIG. 2A) or using murine TNF-specific enzyme linked immunoabsorbent assay (ELISA) kit (FIG. 2B) as described in Example 3. Results shown are average of quadruplicate values (±SD in B) from one of two experiments.
Figure 2B:
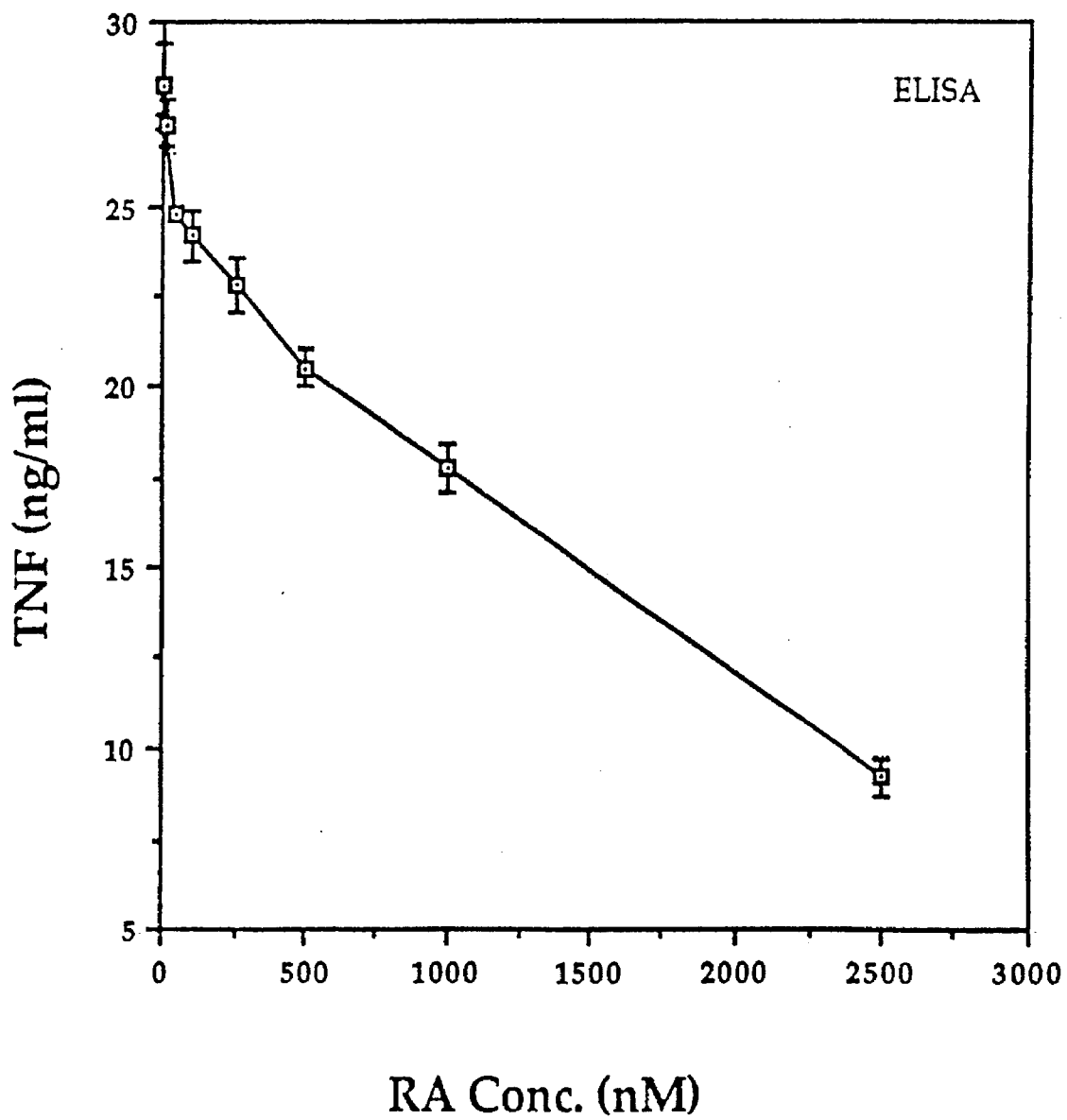

FIG. 2 demonstrates a dose-related inhibition of TNF secretion by ATRA. ATRA inhibited TNF secretion starting at $10^{-8}$M and maximum inhibition was seen at 1–2.5× $10^{-6}$M. Similar results were obtained in two other independent experiments. In order to rule out the possibility that decreased TNF activity in ATRA-treated cultures was not due to the accelerated release of soluble TNF receptor, culture supernatants were subjected to ELISA for TNF protein determination. FIG. 2B clearly shows that the decrease in TNF activity was due to a decrease in TNF protein secretion. Furthermore, ATRA treated macrophages showed no alteration in binding to $^{125}$I-labelled TNF.

Figure 3A:
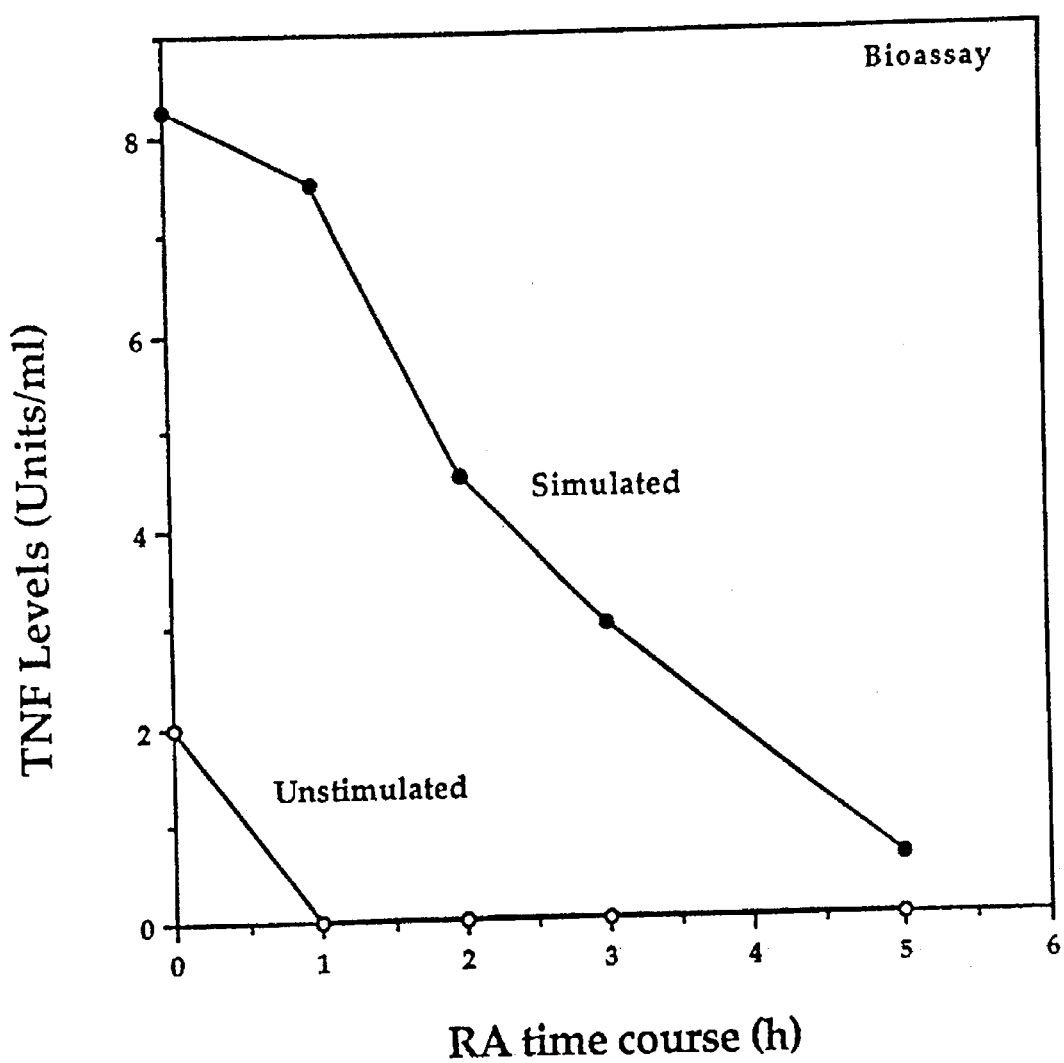
FIG. 3 shows the time-dependent inhibition of TNF production by ATRA from activated peritoneal macrophages. Macrophage monolayers were incubated for a total of 5 hours in presence of medium alone (0) or medium containing activators (IFN-g+LPS, •). ATRA (1 µM) was added to different cultures at various times prior to harvesting the supernatants. Cell-free supernatants were then used to determine the TNF levels in a bioassay (FIG. 3A) or by ELISA (FIG. 3B). Results shown are an average of triplicate values form one of two experiments.
Figure 3B:
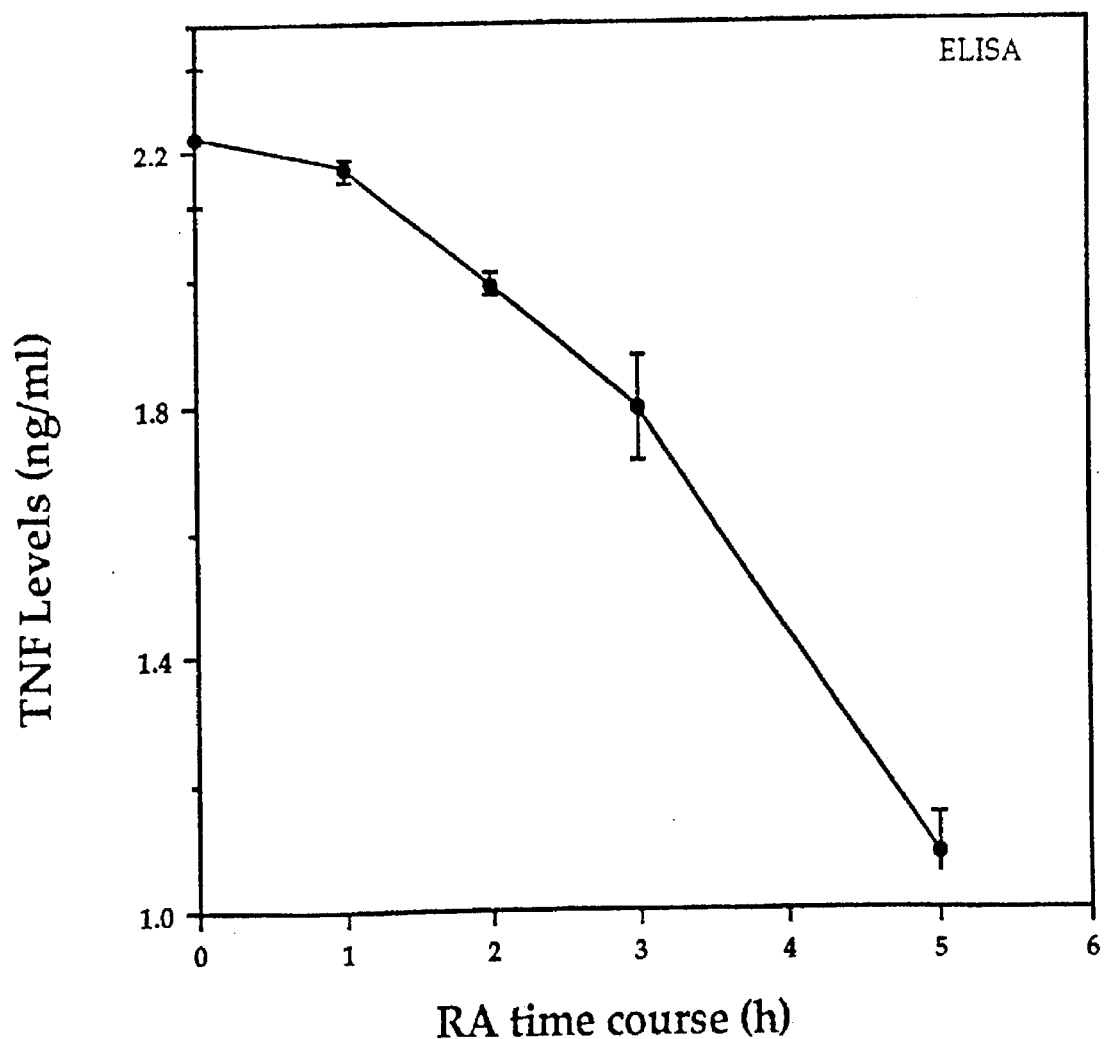

FIG. 3 illustrates that a continuous presence of ATRA throughout the culture period during the activation phase was essential for ATRA to exert maximal inhibition of TNF release by activated macrophages. Thus, inhibition of TNF production could be reached in a time-dependent manner by delaying addition of ATRA to the macrophage cultures, following initiation of their activation with IFN-γ and LPS.

EXAMPLE 6

Effect of ATRA in RAW 264.7 Cells

Figure 4:
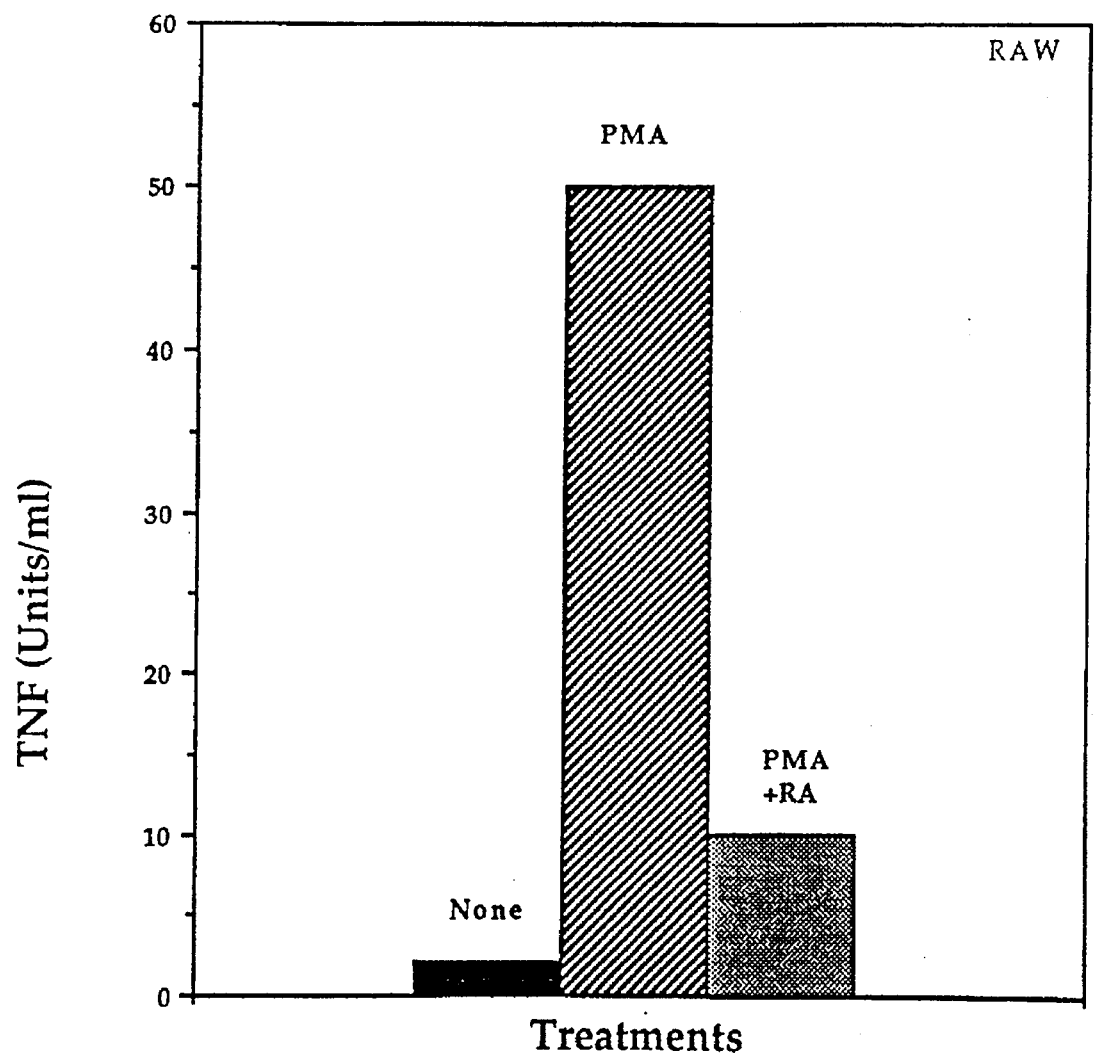
FIG. 4 shows the effect of ATRA-treatment on TNF production from RAW-264.7 cells. RAW 264.7 cells during exponential-phase of cell growth, were cultured in presence or absence of phorbol ester (TPA, 20 ng/ml) and/or ATRA (1 µM) in 24-well plates ($2 \times 10^6$ cells/well). Forty-eight hours later, cell-free supernatants were harvested and assayed for TNF activity. Results are an average of triplicate values form one of the three similar experiments.

Several transformed cell lines have been shown to produce TNF in response to their activation with tumor promoter phorbol ester (TPA). To ascertain whether ATRA-mediated suppression of TNF is a generalized phenomenon, RAW-264.7, a murine macrophage-like cell line, was examined for its ability to produce TNF in response to TPA (10 μg/ml) in presence and absence of ATRA (1 μM). FIG. 4 demonstrates that ATRA is a potent inhibitor of TPA-triggered TNF production in RAW-264.7 cells. The decrease in TNF activity in culture supernatants was associated with a parallel decrease in the amount of TNF protein as determined by murine-TNF specific ELISA kit.

EXAMPLE 7

ATRA Inhibition of Nitric Oxide Production from Activated Macrophages

Figure 5:
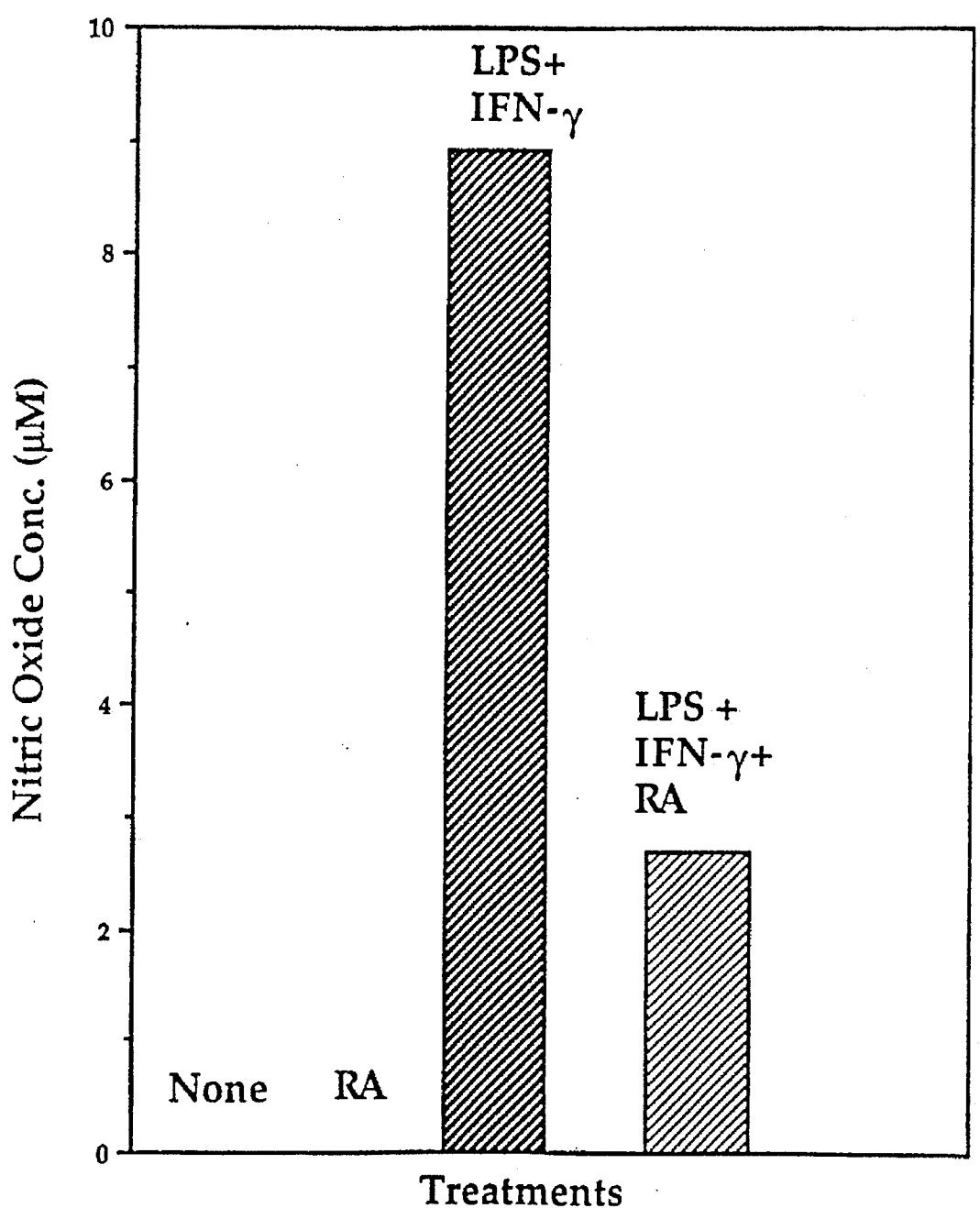
FIG. 5 shows the inhibition of nitric oxide production by ATRA from in vitro activated murine peritoneal macrophages. Two million cells were incubated in presence or absence of activators with or without 1 µM ATRA. Twenty-four hours later, cell-free supernatants were harvested and assayed for nitric oxide levels as described in Example 4. Results are an average of quadruplicate values from a representative experiment.
Figure 6A:
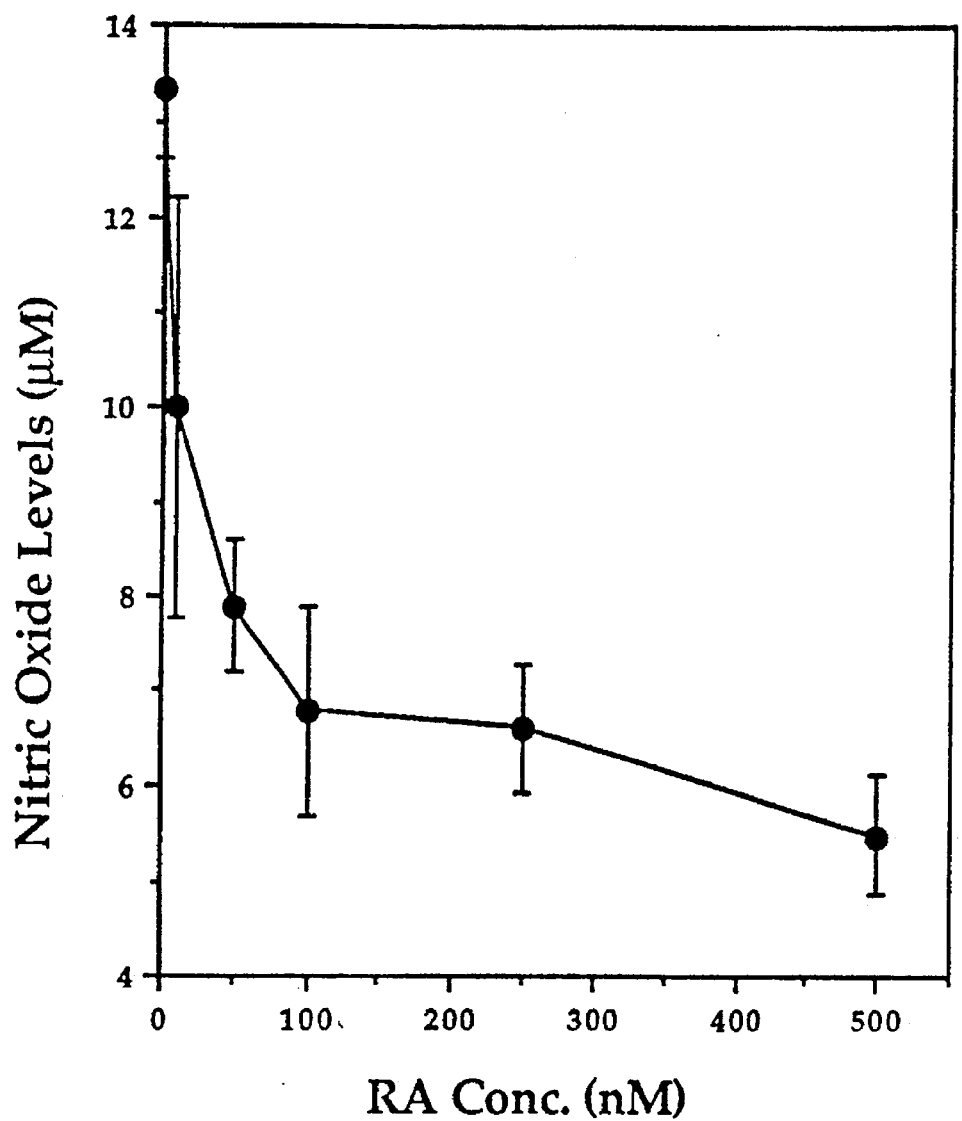
FIG. 6 shows the dose-dependent and time-dependent inhibition of nitric oxide production by ATRA from peritoneal macrophages. Macrophage monolayers were activated with IFN-g (10 U/ml) and LPS (100 ng/ml) along with ATRA at indicated dose levels (FIG. 6A). Alternatively, ATRA was added at various time intervals prior to harvesting the supernatants (FIG. 6B) after 24 hours of activation period. Cell-free supernatants were assayed for nitric oxide production. Results are an average of quadruplicate values ±SD.
Figure 6B:
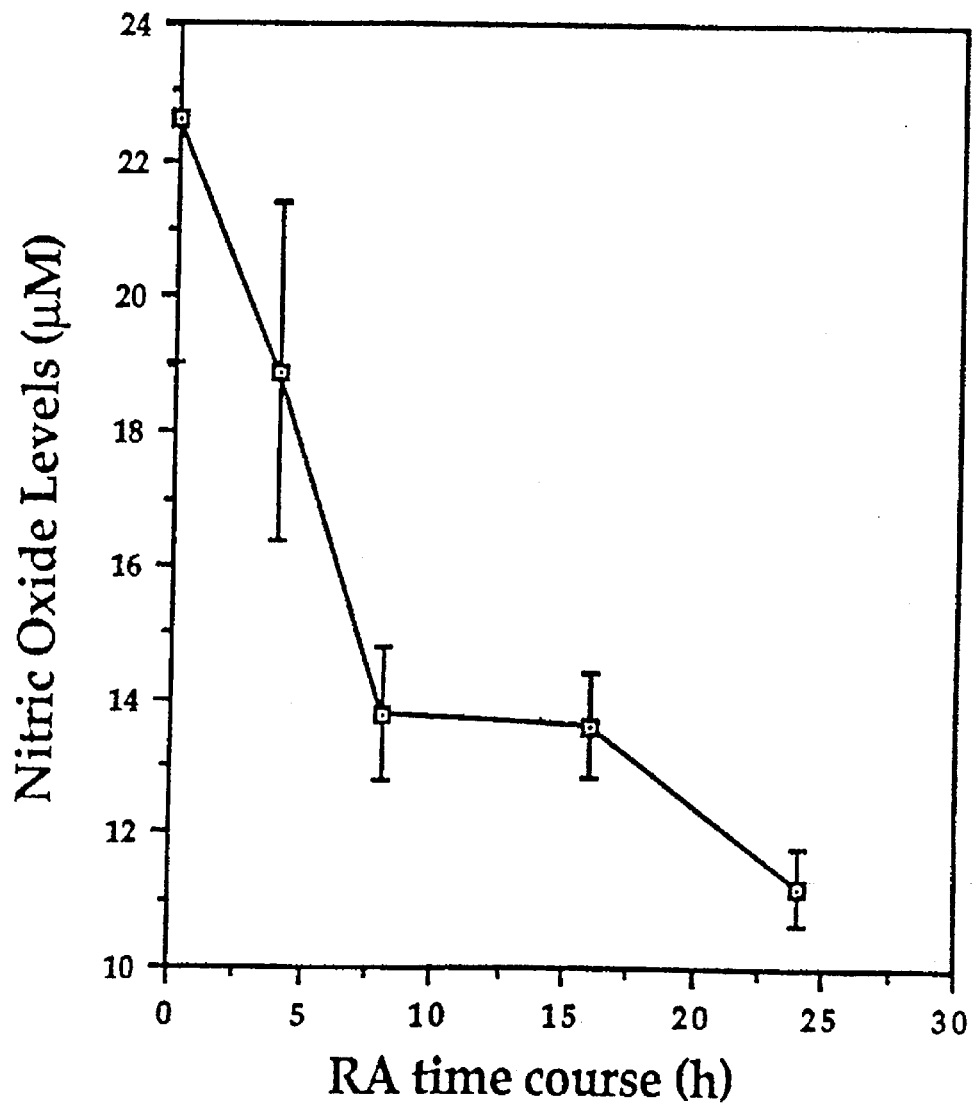

As shown in FIG. 5, activation of resident peritoneal mouse macrophages with IFN-g and LPS in presence of ATRA, greatly decreased the nitric oxide production in culture supernatants. The effect of ATRA on nitric oxide production by activated macrophages was dose-dependent (FIG. 6A) and time-dependent (FIG. 6B). Thus, the inhibitory effect was evident at a physiological dose level of ATRA (10 nM) and became maximal at a pharmacologically achievable dose level (1 μM).

Similar to its effect on TNF production, continuous presence of ATRA was needed throughout the activation period in order to exert optimum inhibitory effect on nitric oxide production. Thus, addition of ATRA at various concentrations (FIG. 6A) and at various time intervals (FIG. 6B) after initiation of the activation with IFN-g/LPS, showed a time-dependent increase in accumulation of nitric oxide in the culture supernatants.

Macrophages play a critical role in host defense against infectious agents and tumors. They also participate in regulation of several immune functions, such as inflammatory responses. Most of these responses are modified through the production of soluble mediators called cytokines. The present invention describes the down regulatory effect of ATRA and its analogues (retinoids) on LPS/IFN-g triggered in vitro production of TNF and nitric oxide by mouse peritoneal macrophages. The suppression of TNF and nitric oxide was observed with as little dose of ATRA as 10 nM, a physiological concentration. The observed effects, therefore, are of physiological significance. The plasma concentration of ATRA can be achieved in micromolar levels following ATRA administration. At this concentration, 75% to 90% of TNF production was blocked by activated macrophages (FIG. 1).

TNF and nitric oxide have both been shown to play a key role in macrophage-mediated inflammatory responses as well as in killing of tumor cells. Endogenous and exogenous retinoids (including ATRA) are potent inhibitors of activated macrophage-mediated cytostasis against murine adenocarcinoma (EMT-6) target cells. Arginine-dependent nitric oxide$^{2-}$/nitric oxide$^{3-}$ production by activated macrophages, on the other hand, has been shown to induce inhibition of mitochondrial respiration that eventually lead to growth inhibition of EMT-6 cells.

The observed inhibitory effect of ATRA on TNF and nitric oxide production were not due to their effect on prostaglandin production. ATRA, at applied concentrations, had no effect on prostaglandin E production by activated macrophages. Similarly, concentrations of ATRA (up to 2.5 μM) used in the methods of the present invention, showed no apparent toxic effects on cultured macrophages. TNF, in combination with other cytokines, such as IFN-g is capable of inducing nitric oxide production by macrophages.

EXAMPLE 8

Materials

RPMI-1640 and DMEM were obtained from Whittaker MA Bioproducts (Walkersville, Md.). Fetal bovine serum (FBS) and gentamicin were from GIBCO (Grand Island, N.Y.). Bacteria-derived recombinant human TNF (specific activity 5×10$^7$ U/mg) was kindly supplied by Genentech, Inc. (South San Francisco, Calif.). Carrier-free Na-$^{125}$I was purchased from Amersham (Arlington Heights, Ill.); PD-10 (prepacked Sephadex G-25 medium) columns were from Pharmacia Fine Chemicals (Piscataway, N.J.); iodogen and gelatin were from Sigma Chemical Co. (St. Louis, Mo.). The highly purified form of the recombinant extracellular domains of TNF receptors p60 and p80 were provided by Dr. T. Kohno (Synergen, Boulder, Colo.). Polyclonal antibodies were raised in rabbits against each type of receptor and purified by receptor-affinity chromatography. All-trans retinoic acid was purchased from Kodak Fine Chemicals. Retinol, 9-cis retinoic acid, TTNPB and 3-methyl-TTNPB, were provided by Dr. Peter Davis (University of Texas Health Science Center, Houston, Tex.).

EXAMPLE 9

Cell Culture

U-937 (histiocytic lymphoma, CRL 1593) and THP-1 (acute monocytic leukemia, TIB 202) cell lines used in this study were obtained from American Type Cell Culture Collection (Rockville, Md.). These cells were grown in RPMI-1640 supplemented with 10% FBS, and 50 mg/ml gentamicin.

EXAMPLE 10

Retinoic Acid Treatment

Solutions of retinoic acid (1 mM), retinol (1 mM), 9-cis retinoic acid (5 mM), TTNPB (5 mM), and 3-methyl-TTNPB (5 mM) were prepared in dimethyl sulfoxide (DMSO) and then diluted in the appropriate medium. Cells ($0.2-0.5\times10^6$/ml) were incubated with retinoic acid at 37° C. for 0–24 hours in 12-well plates or in T25 tissue culture flasks in serum-free medium. The medium was then removed, and the cells washed, counted for viability, and then examined for TNF receptors. An appropriate DMSO control was run wherever necessary.

EXAMPLE 11

Receptor Binding Assays

In the receptor binding assays, TNF was labeled with Na-$^{125}$I using the Iodogen method. Briefly, 10 mg of TNF in a 20 ml volume was placed onto a film of 50 mg of Iodogene and incubated for 10 minutes at 4° C. in the presence of 1 mCi of carrier-free Na-$^{125}$I. Free iodine was removed by gel filtration on a PD-10 (Sephadex G-25) column equilibrated with PBS contained 0.1% gelatin. More than 96% of the iodine in the final product was incorporated in the protein as determined by trichloroacetic acid (TCA) precipitation. The specific activity of the labeled TNF ranged from 20–30 mCi/mg.

Binding assays were performed in flexible 96-well plates precoated with 0.2 ml of FBS for 24 hours at 4° C. The binding medium (RPMI-1640) contained 10% FBS. Cells ($0.4-0.5\times10^6$/0.1 ml) were incubated with $^{125}$I-TNF in the absence (total binding) or in the presence of 100 nM unlabeled ligand (nonspecific binding) for 1 hour at 4° C. The cells were washed three times with ice-cold medium (PBS containing 0.1% BSA) at 4° C., and the cell-bound radioactivity was determined in a g-counter (Cobra-Auto-Gamma, Packard Instrument Co.). All determinations were performed in triplicate.

Specific binding of the $^{125}$I-labeled TNF was calculated by subtraction of nonspecific binding from the total binding. Inhibition of specific binding by retinoic acid was calculated from the specific binding obtained from the untreated cells (100%). The dissociation constant (Kd) and the number of receptors were calculated by Scatchard analysis.

EXAMPLE 12

Covalent Cross-Linking of TNF to Cell Surface Receptors

The cross-linking procedure was carried out according to the previously described method of Stauber, et at., *J Biol Chem*, 264(6):3573–3576 (1989). Briefly, cells ($20\times10^6$) were incubated with 2.5 nM $^{125}$I-labeled TNF in 1 ml RPMI-1640 for 1 hour at 4° C., washed three times with ice-cold PBS to remove unbound ligand, and then treated with 0.1 nM (final concentration) ethylene glycol-bis (succinimidyl succinate) (EGS), the cross-linking reagent. After a 45 minute incubation at room temperature, EGS was quenched by a 10 minute incubation with 20 mM ammonium chloride (final concentration). The cells were washed with ice-cold PBS and solubilized with solubilization buffer (50 mM Tris, pH 7.5) supplemented with aprotinin (2 mg/ml), phenylmethylsulfonyl fluoride (1 mM), leupeptin (2 mg/ml), NP40 (0.5%), sodium chloride (200 mM) and β-mercaptoethanol (0.1%). After a 10-minute incubation at 4° C., the samples were centrifuged and the supernatants were analyzed on 7% SDS-PAGE. The gel was dried and exposed to a Phosphorimager screen (Molecular Dynamics, Sunnyvale, Calif.), and the image was recorded and quantitated using "Image Quant" software.

EXAMPLE 13

Receptor-Mediated Internalization of TNF

The ligand internalization studies were carried out according to the procedure as described previously by Higuchi, et al., *45th Annual Symposium on Fundamental Cancer Research*, 1992. Briefly, U937 cells ($0.5\times10^6$ cells/ml) were incubated either with or without RA (1 mM) for 24 hours at 37° C. in serum-free medium. The cells were then washed and incubated in a fresh medium for 2 hours at 4° C. with $0.5\times10^6$ cpm/ml of $^{125}$I-labeled TNF, and then unbound $^{125}$I-TNF was removed by three washes with cold PBS containing 0.1% BSA. The kinetics of internalization of TNF was examined by incubating the cells with fresh medium at 37° C. At indicated times medium was removed and counted for radioactivity in the gamma counter. The cell-surface bound TNF was luted from cells by acid washing twice (0.2M acetic acid and 0.5M sodium chloride, pH 3.0) at different times and counted. For determination of internalized TNF (the acid-nondissociable fraction), acid-washed cells were solubilized in 0.5M sodium hydroxide and then counted. The acid wash procedure used to remove the cell surface-bound TNF did not significantly affect cell viability as determined by trypan blue exclusion.

EXAMPLE 14

Shedding of TNF Receptor

U-937 ($0.5\times10^6$/ml) cells were incubated with or without retinoic acid at 37° C., and culture supernatants were removed after centrifugation. The amount of soluble TNF receptors was assayed by using a TNF receptor enzyme-linked immunological biological assay (ELISA) kit (Hoffmann-La Roche, Basel, Switzerland; p60 kit # S-0740 and p80 kit # S-2140). Briefly, 0.2 ml of monoclonal anti-p60 or anti-p80 receptor antibody (0.5 mg/ml) in 100 mM sodium phosphate, pH 6.5, was added to a 96-well ELISA plate (Nunc 468667, Neperville, Ill.) and incubated at room temperature overnight. Then wells were washed three times with water, and 0.2 ml of 200 mM Tris-HCl pH 7.5 containing Kathon MW/WT and 0.1% BSA was added. After overnight incubation, wells were again washed three times; then test samples or standard solutions of recombinant soluble p60 and p80 were added. After overnight incubation at room temperature, wells were washed four times with 0.05% Tween 20 in $H_2O$ and twice with $H_2O$ alone. For detection, 0.2 ml of 30 mM potassium citrate buffer pH 4.1 containing Kathon MW/WT, 500 nM 3,3', 5,5'-tetramethylbenzidine and 4 mM $H_2O_2$ was added and the solution incubated for 30 minutes. To stop the reaction, 50 ml of 1M sulfuric acid was added. Absorbance at 450 nM was measured and the amount of p60 and p80 receptor in the test samples was evaluated from the standard curve.

EXAMPLE 15

Northern Blot Analysis of the Expression of p60, and p80 mRNAs

U-937 cells ($0.5 \times 10^6$/ml) were treated with 1 mM retinoic acid for different times. Total cellular RNA was extracted from cells as is well known in the art. For Northern blot analysis, RNA samples (20 mg) were denatured with formamide and formaldehyde and electrophoresed in 0.8% agarose gel containing 0.67M formaldehyde at 75 V for approximately 3 hours. RNA was alkali-transferred to Hybound $N^+$ nylon membrane (Amersham Corp., Arlington Heigths, Ill.). After alkali transfer, the membrane was rinsed with 2×SSC (1×SSC:0.15M sodium chloride, 0.015M sodium citrate, pH 7.0). It was prehybridized at 65° C. for 1 hour in hybridization buffer containing 7% SDS and 1 mM EDTA in 0.5M sodium phosphate buffer, pH 7.2. The membrane was then hybridized for 16–20 hours with $^{32}P$-labeled cDNA probes for p60 and p80 (approximate specific activity, $5-10 \times 10^8$ cpm/mg DNA) in the hybridization buffer, plus denatured salmon sperm DNA (0.2 mg/ml). After hybridization the membrane was washed twice with 2×SSPE (1×SSPE:0.18M NaCl, 0.01M sodium phosphate, and 1 mM EDTA) containing 0.1% SDS at room temperature, followed by another wash with 1×SSPE containing 0.1% SDS at 65° C. The blots were then exposed to phosphorimager screen (Molecular Dynamics, Sunnyvale, Calif.), and the images were recorded and quantitated using "Image Quant" software. To demonstrate the equal loading of lanes, the probes were stripped off the membrane by washing the filters twice with 0.5% SDS at 95° C. for 30 minutes. The membrane was then hybridized with a cDNA probe for glyceraldehyde 3-phosphate dehydrogenase (GAPDH).

EXAMPLE 16

RA Down-Regulates Cell Surface Expression of TNF Receptors

Figure 7A:
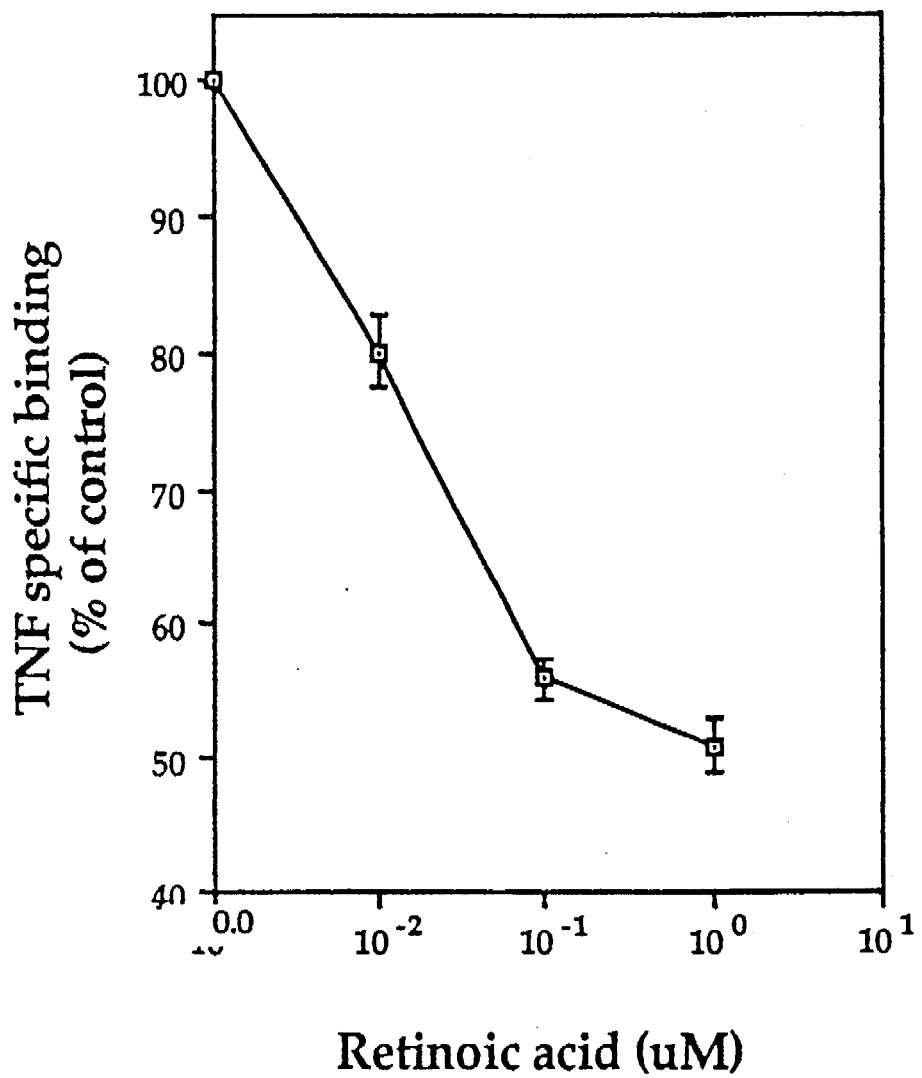
FIG. 7 shows a dose-(FIG. 7A) and time-(FIG. 7B) dependent modulation of TNF receptors by retinoic acid in U-937 cells. Cells ($0.5 \times 10^6$/ml) were incubated with different concentrations of retinoic acid at 37° C. for 24 hours (FIG. 7A) or with 1 mM of RA for different times at 37° C.
(FIG. 7B) in serum-free medium. Thereafter, cells were washed, and counted, and inhibition of TNF binding was determined as described under. All determinations were made in triplicate.
Figure 7B:
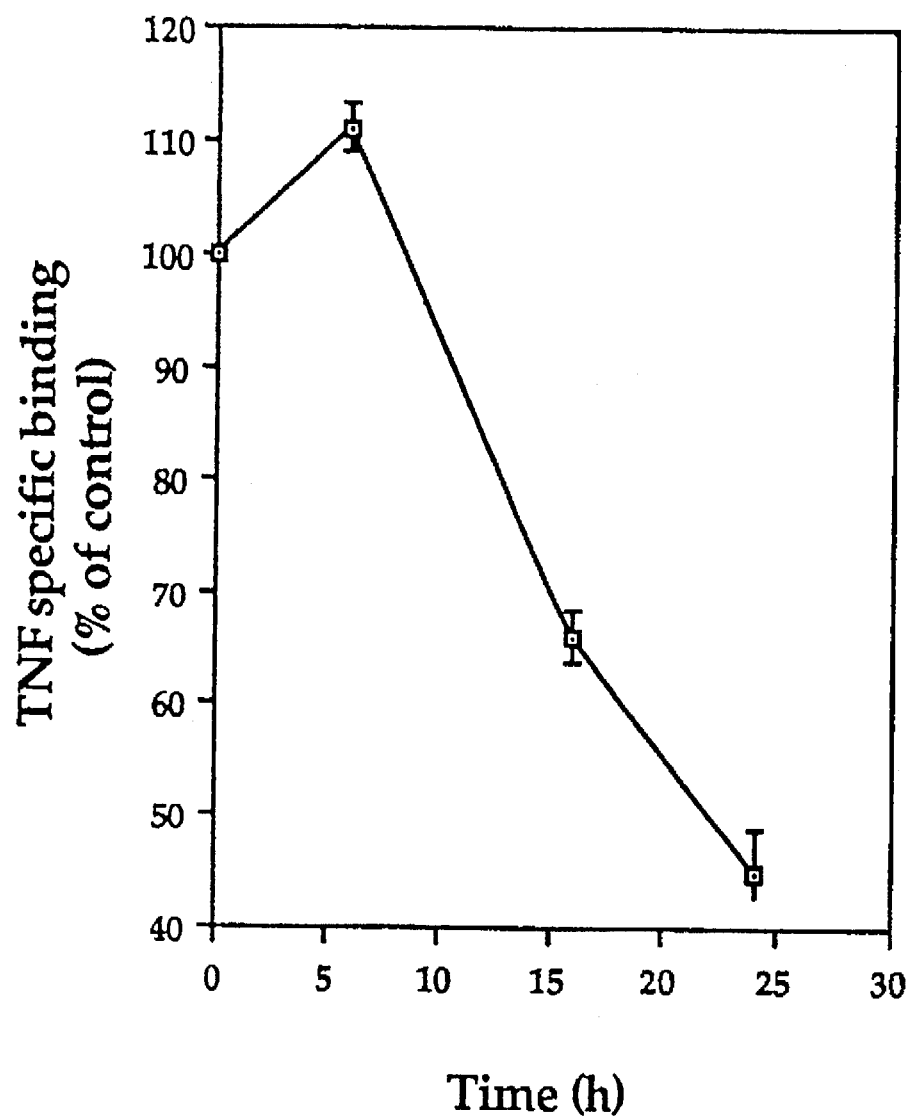

To examine the effect of retinoic acid on TNF receptors, U-937 cells were treated with different concentrations of retinoic acid at 37° C. for 24 hours, washed, and then analyzed for cell surface expression of TNF receptors (FIG. 7A). Retinoic acid decreased the specific binding of $^{125}I$-labeled TNF on U-937 cells in a dose-dependent manner. The maximum decrease (approximately 50%) in binding was observed when cells were treated with 1 mM retinoic acid. This concentration had no effect on the viability of U-937 cells, as determined by cell counting or by [$^3H$]-thymidine incorporation (data not shown). The decrease of TNF receptors by retinoic acid was also not due to an effect on protein synthesis, as evaluated by [$^3H$]-leucine incorporation (data not shown). Next, the time-course of down-regulation of TNF receptors on U-937 cells by retinoic acid was shown. The cells were exposed to 1 mM of retinoic acid at 37° C. for different times and then assayed for specific binding of $^{125}I$-TNF. Binding decreased in a time-dependent manner throughout the retinoic acid treatment (FIG. 7B). A 58% decrease in binding was observed after 24 hours. Concerning the effect of retinoic acid (1 mM for 24 hours) on TNF receptors in acute monocytic leukemia cell line, THP-1, a 66% decrease in specific binding of TNF (1000 cpm vs 342 cpm) was observed.

Figure 8A:
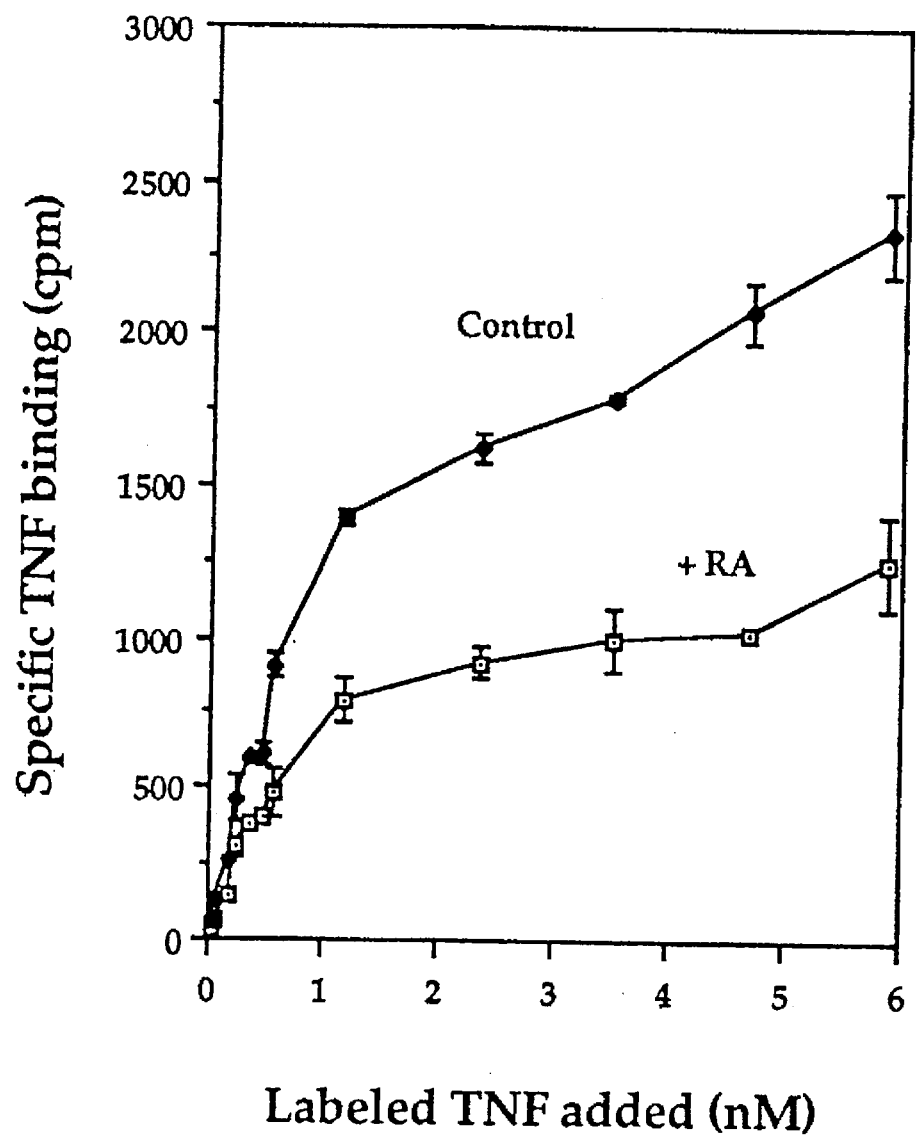
FIG. 8 shows the competitive TNF receptor binding (FIG. 8A) and Scatchard plot analysis (FIG. 8B) of the U-937 cells exposed to retinoic acid. Cells ($0.5 \times 10^6$/ml) were incubated without or with 1 mM of retinoic acid in serum-free medium at 37° C. for 24 hours, and then washed, and counted, and TNF binding was measured with different concentrations of labeled TNF in the presence (nonspecific binding) and absence (total binding) of 100 nM unlabeled TNF. All measurements were carried out in triplicate.
Figure 8B:
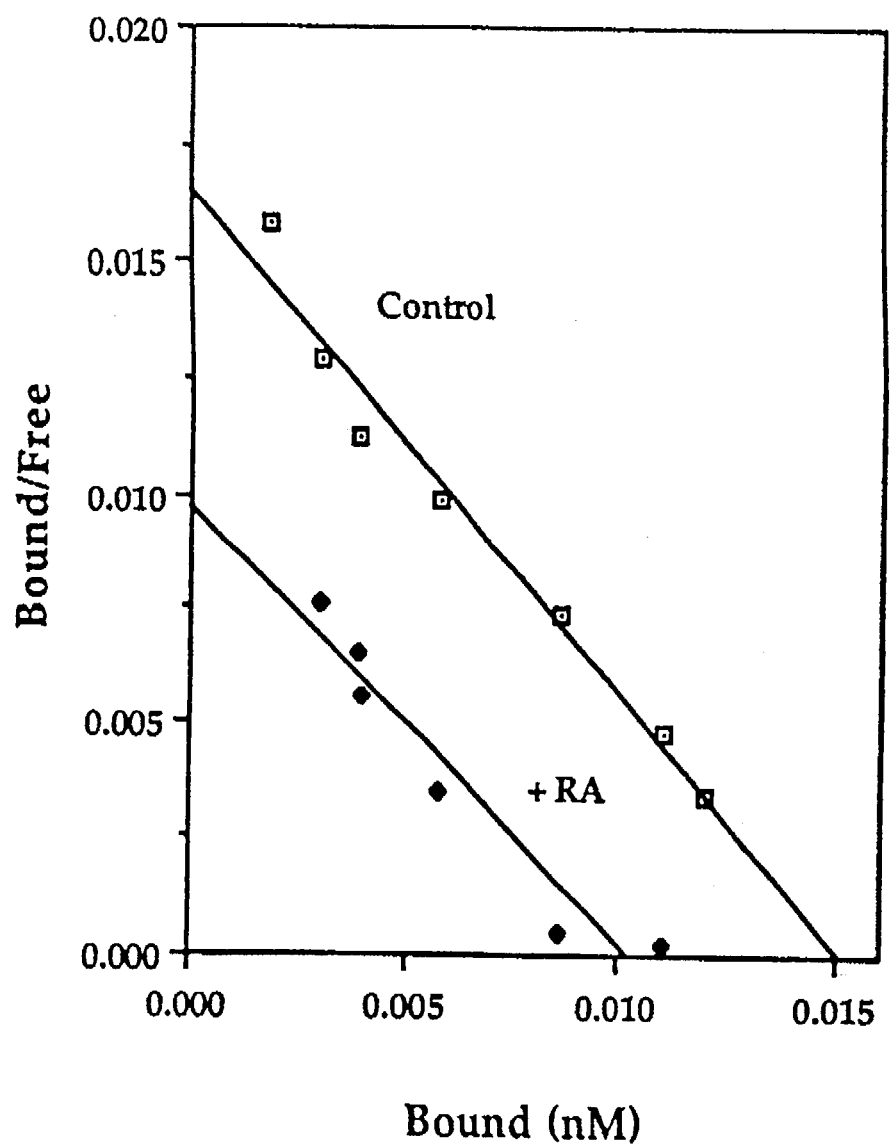

Scatchard analysis was used to determine the effects of retinoic acid treatment on the number and/or binding affinity of TNF receptors. The cells were treated with 1 mM retinoic acid for 24 hours at 37° C., washed, and then analyzed for receptor binding characteristics by incubating cells with varying amounts of $^{125}I$-TNF in the absence or presence of a 100-fold excess of unlabeled TNF (FIG. 8A). For untreated cells, the receptor numbers/cell and dissociation constant ($K_d$) were 4554 sites/cell and 1.0 nM, respectively. For cells treated with 1 mM retinoic acid, the values were 3044 receptor numbers/cell and 1.05 nM, respectively. Thus, retinoic acid decreased the number of TNF receptors, whereas the affinity of the receptors did not change significantly (FIG. 8B).

Figure 9A:
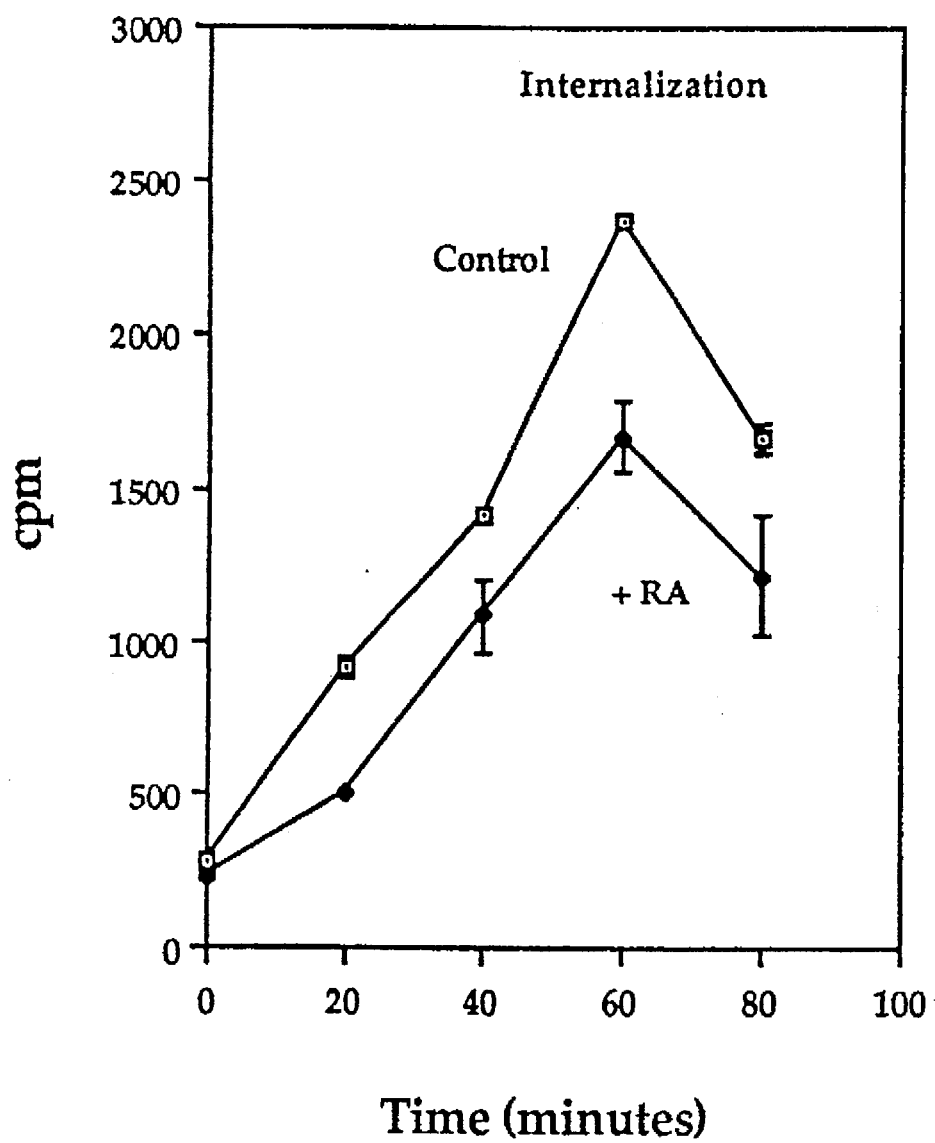
FIG. 9 shows the effect of retinoic acid on the rate of internalization (FIG. 9A) and the rate of disappearance (FIG. 9B) of labeled TNF from the surface of U937 cells. $0.5 \times 10^6$ cells were treated with RA (1 mM) for 24 hours, washed, and then incubated for 2 hours with labeled TNF at 4° C., the excess ligand washed off and then the cells incubated at 37° C. for the indicated time periods with 0.1 ml of medium. At the indicated time, cells were washed and the rate of dissociation (acid-dissociable) and internalization (acid-nondissociable) of labeled TNF determined. Results were mean ±SD for triplicate determinations.

To demonstrate that the down-modulation of TNF receptors by retinoic acid affects ligand internalization, the rate of internalization and the dissociation of the ligand from the cell surface was shown. FIG. 9 clearly indicates that retinoic acid decreased both the internalization of the ligand into the cells (FIG. 9A) and dissociation of the ligand from the cell surface (FIG. 9B). Thus, retinoic acid down-modulates the TNF uptake by the cells.

Figure 10:
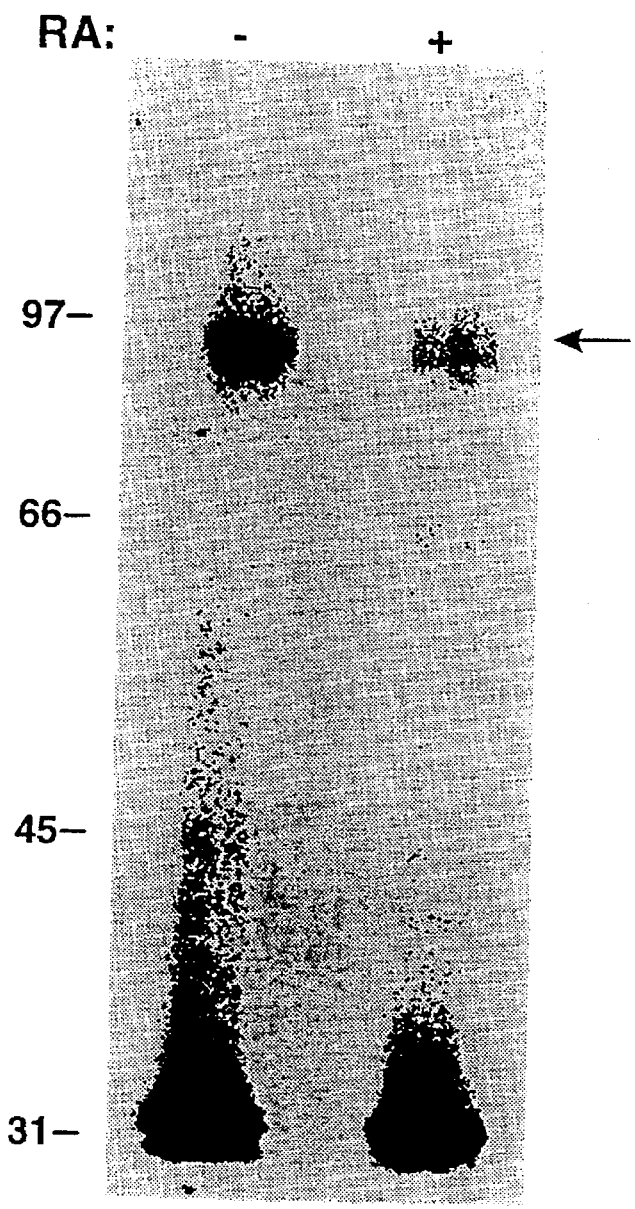
FIG. 10 shows the effect of retinoic acid treatment of the U937 cells on the receptor-ligand crosslinking. $0.5 \times 10^6$ cells/ml were incubated either with or without 1 mM RA for 24 hours at 37° C. Cells were then rinsed, performed the receptor binding, crosslinked the receptor ligand complex with EGS and then analysed by SDS-PAGE as described.

To further confirm the retinoic acid-mediated down-modulation of TNF receptors, receptor-ligand cross-linking studies on U-937 cells were carried out. $^{125}I$-labeled TNF was cross-linked to the cell surface receptors on control and retinoic acid-treated cells using EGS, and the ligand-receptor complexes were visualized following SDS-PAGE (FIG. 10). A single band with a molecular mass of 98 kDa in untreated U-937 cells was observed. A band with the same molecular mass was also observed in retinoic acid-treated cells, but computer-assisted densitometry showed that the amount of cross-linked TNF-receptor complex was 50% of the control value (FIG. 10). These studies demonstrate the down-regulation of the p80 form of the tumor necrosis factor receptor by retinoic acid but it was not possible to visualize the p60 receptor in either control or retinoic acid-treated cells.

EXAMPLE 17

RA Decreases the mRNAs of TNF Receptors

Figure 11:
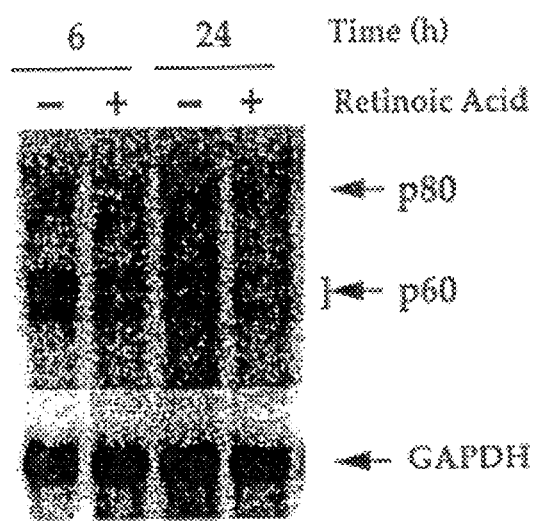
FIG. 11 shows the effect of retinoic acid on the steady state levels of the mRNA for p60 and p80 forms of the TNF receptor. For each point $10 \times 10^6$ U-937 cells at $0.5 \times 10^6$/ml were incubated either with or without 1 mM retinoic acid for 6 hours and 24 hours at 37° C. either in the absence of serum. The total RNA was isolated, electrophoresed, and hybridized with specific probes.

Whether down-regulation of the cell surface expression of TNF receptors was accompanied by a decrease in receptor mRNA levels was investigated. Northern blot analysis (FIG. 11) of control and retinoic acid treated U-937 cells, showed decrease in the mRNAs coding for the p60 and p80 forms of the TNF receptor. Therefore, the down-regulation of the cell surface expression of TNF receptors, induced by retinoic acid, was a consequence of a decrease in mRNA levels.

EXAMPLE 18

RA Down-Regulates Both the p60 and p80 Forms of TNF Receptors

Figure 12:
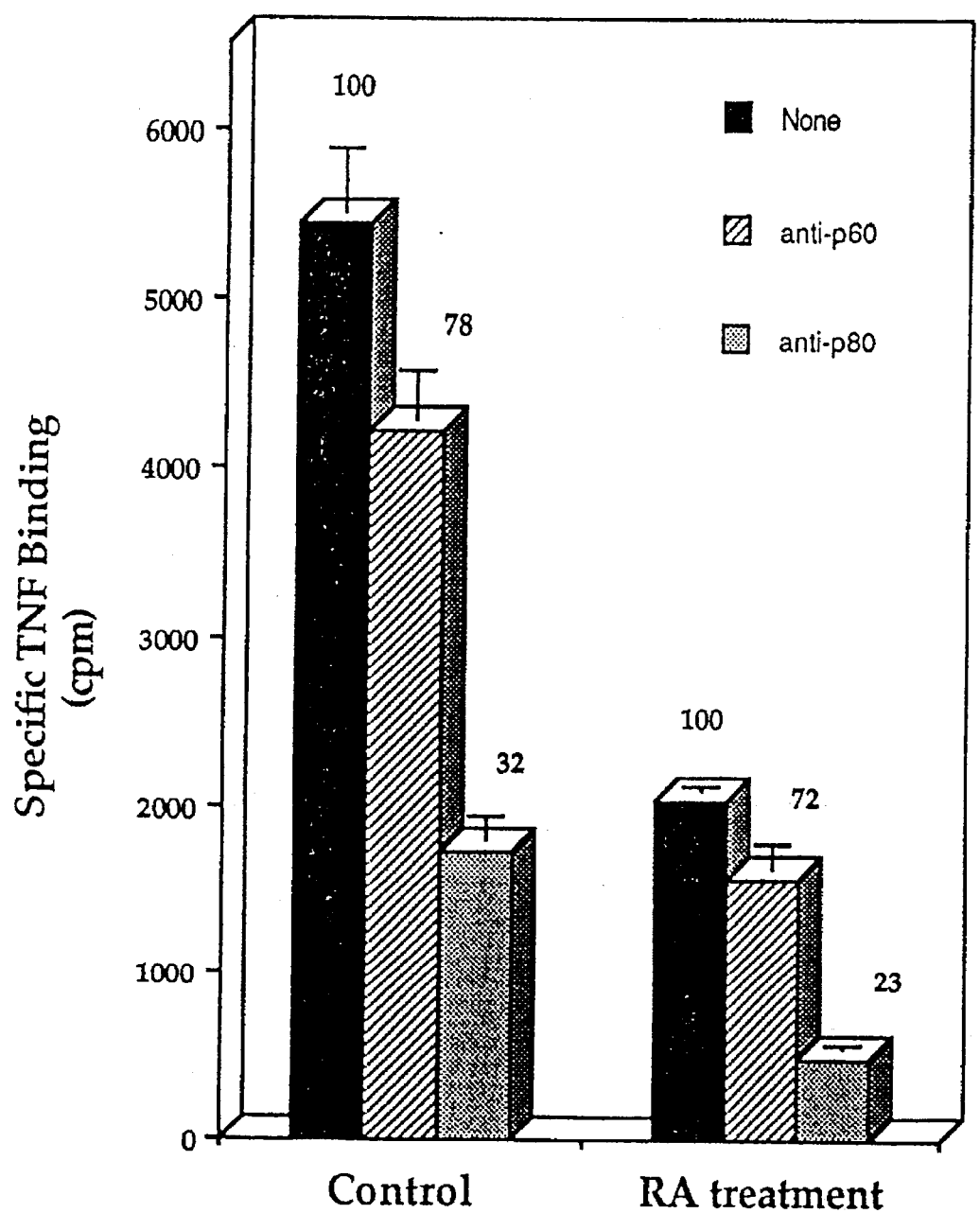
FIG. 12 shows the effects of retinoic acid on the cell surface expression of p60 and p80 form of TNF receptors in U-937 cells. Cells ($0.5 \times 10^6$/ml) were incubated with 1 mM retinoic acid for 24 hours at 37° C. in serum-free medium. Thereafter, the cells were washed and examined for p60 and p80 form of the TNF receptors by using anti-p60 or anti-p80 antibodies. All determinations were made in triplicate. The numbers on top are the percentages.

60–80% of the total TNF-binding sites on U-937 cells can be attributed to the p80 form of the TNF receptor, and p60 receptors constitute the other 20–40% of the binding. To determine which receptor was influenced by retinoic acid, receptor-specific antibodies were used. FIG. 12, indicates that retinoic acid down-modulated both forms of the TNF receptors to a similar extent.

EXAMPLE 19

Down-Modulation of TNF Receptors by RA Is Not Due to its Shedding

The possibility that retinoic acid decreases the number of cell surface TNF receptors by causing their release (shedding) into the medium was also investigated. U-937 cells were treated with 1 mM of retinoic acid at 37° C. for 6 hours and 24 hours. The shed form of the TNF receptor in the culture medium was analyzed by an ELISA kit. Retinoic acid treatment had no effect on the shedding of the p60 and p80 forms of the receptor (data not shown).

EXAMPLE 20

RA Analogues Down-Regulate TNF Receptors on U-937 Cells

Figure 13:
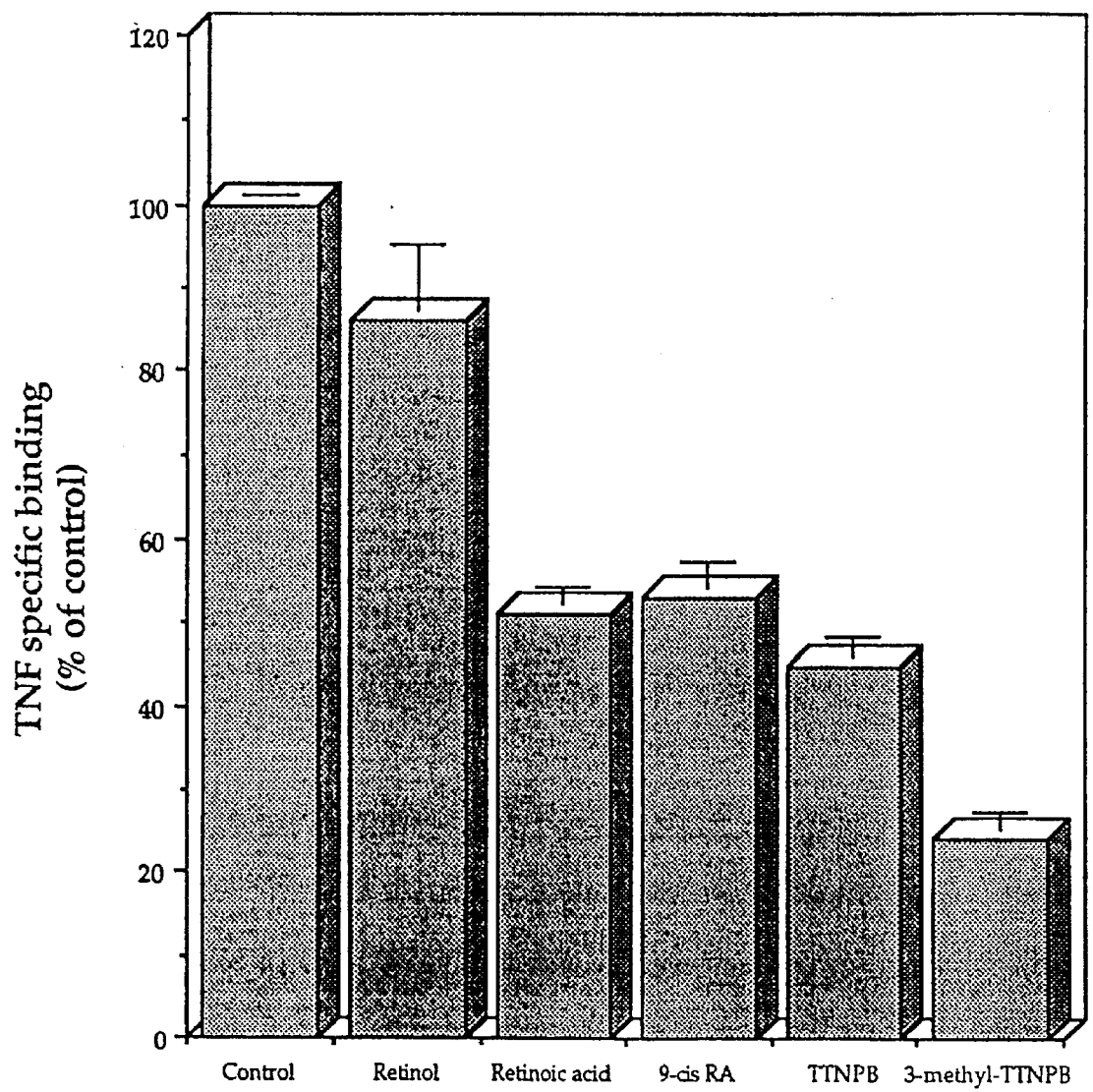
FIG. 13 shows the modulation of TNF receptors by different retinoic acid analogues in U-937 Cells. Cells ($0.5 \times 10^6$/ml) were incubated with 1 mM each of retinol, retinoic acid, 9cis, TTNPB and 3-methyl-TTNPB at 37° C. for 24 hours in serum-free media. Thereafter, the cells were washed and counted, and TNF binding assay performed. Each bar represents the average of three determinations.

The intracellular effects of retinoic acid were mediated by two families of retinoid receptors, retinoic acid (RARs) and retinoic X (RXRs) receptors. While all-trans-retinoic acid binds to both RAR and RXR, 9-cis-RA has much higher affinity for the RXR family. Similarily, TTNPB and 3-methyl-TTNPB have higher affinities for RAR and RXR, respectively. To demonstrate the role of different retinoid receptors in TNF binding, U-937 cells were treated with different retinoid analogues (1 mM) for 24 hours and then examined them for TNF receptors. FIG. 13 illustrates that under identical conditions 3-methyl-TTNPB was maximally effective (80%) and retinol was least effective (10%) in decreasing TNF receptors. There was no significant difference between cis- and all-trans- forms of retinoic acid (45–50%), and TTNPB was as effective as all trans-RA. Thus, both classes of retinoid receptors appear to be involved in the modulation of TNF receptors on U-937 cells.

The present invention demonstrates that all-trans retinoic acid decreases the cell surface expression of TNF receptors on U-937 cells. The decrease in TNF receptors by retinoic acid was not unique to U-937 cells but was also observed with another myeloid cell line, THP-1. Scatchard analysis revealed that retinoic acid down-regulated TNF receptor number without significantly changing the receptor affinity. Furthermore, both forms of the TNF receptor were down-modulated by retinoic acid. Studies with analogues of retinoic acid indicated that the down-regulation of TNF receptor was mediated through both RAR and RXR forms of the retinoic acid receptor.

The present invention indicates that both types of TNF receptor in U-937 cells are down-modulated by retinoic acid when treated for 24 hours. In contrast, Winzen et al. showed that retinoic acid treatment of HL-60 cells increased TNF binding. In U-937 cells, the present invention demonstrated changes in TNF receptor levels by binding, receptor-ligand cross-linking and receptor-specific blocking antibodies, and by mRNA analysis.

As shown by the present invention for the modulation of TNF receptors by retinoic acid, the receptors for IL-6, AMF and EGF have also been shown to be downmodulated by retinoic acid. In contrast, the receptors for IL-2, TGF-beta and NGF are increased by retinoic acid. How retinoic acid induces the receptors for some cytokines while down-modulating that of others, is not clear. Since retinoic acid modulates the expression of several different cytokines, it is possible that the expression of cytokines by retinoic acid could in turn lead to the modulation of TNF receptors. The cell surface expression of TNF receptors can be down-regulated by a number of different cytokines including IL-1, granulocyte monocyte colony-stimulating factor and TNF.

There are reports which show that activators of protein kinase C (PkC) down-modulate TNF receptors, and retinoic acid has been shown to induce PkC in certain cells. Therefore, it is possible that the effects of retinoic acid on TNF receptors are mediated through the activation of PkC. This possibility is unlikely, however, since activation of PkC has been shown to cause the shedding of TNF receptors, and no receptor shedding was observed on cells treated with retinoic acid. Furthermore, the kinetics of TNF receptor down-modulation by PkC activators was much more rapid than that observed with retinoic acid. The intracellular processes by which retinoic acid could interfere with the cell surface TNF receptors are probably related to their replacement and/or degradation.

All patents and publications mentioned in this specification are indicative of the levels of those skilled in the art to which the invention pertains. All patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A method of inhibiting the production of tumor necrosis factor, comprising the step of administering to an animal in need of such treatment a pharmacologically effective dose of a retinoic acid compound.

2. The method of claim 1, wherein said retinoic acid compound is selected from the group consisting of all-trans-retinoic acid, 4-hydroxy-retinoic acid, 9-cis-retinoic acid, (E)-4-[2-(5, 6, 7, 8-tetrahydro-2-naphtalenyl)-1-propenyl]-benzoic acid, 3-methyl-(E)-4-[2-(5, 6, 7, 8-tetrahydro-2-naphtalenyl)-1-propenyl]-benzoic acid and 13-cis-retinoic acid.

3. The method of claim 1, wherein said animal is a human.

4. The method of claim 1, wherein said dose said a retinoic acid compound is from about 10 nM and to about 1 µM.

5. A method of inhibiting tumor necrosis factor receptors, comprising the step of administering to an animal in need of such treatment a pharmacologically effective dose of a retinoic acid compound.

6. The method of claim 5, wherein said retinoic acid compound is selected from the group consisting of all-trans-retinoic acid, 4-hydroxy-retinoic acid, 9-cis retinoic acid, (E)-4-[2-(5, 6, 7, 8-tetrahydro-2-naphtalenyl)-1-propenyl]-benzoic acid, 3-methyl-(E)-4-[2 -(5, 6, 7, 8-tetrahydro-2-naphtalenyl)-1-propenyl]-benzoic acid and 13-cis-retinoic acid.

7. The method of claim 5, wherein said animal is a human.

8. The method of claim 5, wherein said dose said a retinoic acid compound is from about 10 nM and to about 1 µM.

9. The method of claim 5, wherein said retinoic acid compound inhibits tumor necrosis factor receptor synthesis.

10. The method of claim 5, wherein said retinoic acid compound inhibits the quantity of tumor necrosis factor receptors.

11. A method of treating a pathophysiological state in an animal in need of such treatment, wherein said state is characterized by production of an undesirable level of tumor necrosis factor, comprising the step of administering a pharmacologically effective dose of a retinoic acid compound and wherein said disease is selected from the group consisting of sepsis, autoimmune diseases, cachexia, cerebral malaria and capillary leak syndrome.

12. The method of claim 11, wherein said retinoic acid compound is selected from the group consisting of all-trans-retinoic acid, 4-hydroxy-retinoic acid and 13-cis-retinoic acid.

13. The method of claim 11, wherein said animal is a human.

14. The method of claim 11, wherein said dose of said retinoic acid compound is from about 10 nM to about 1 µM.

15. The method of claim 11, wherein said autoimmune disease is selected from the group consisting of systemic lupus erythematosus, rheumatoid arthritis and multiple sclerosis.

* * * * *